(12) United States Patent
McCoy

(10) Patent No.: US 11,887,047 B2
(45) Date of Patent: *Jan. 30, 2024

(54) SYSTEM WITH REFRIGERATOR AND SELF-REPORTING CONTAINER

(71) Applicant: WHIRLPOOL CORPORATION, Benton Harbor, MI (US)

(72) Inventor: Richard A McCoy, Stevensville, MI (US)

(73) Assignee: Whirlpool Corporation, Benton Harbor, MI (US)

( * ) Notice: Subject to any disclaimer, the term of this patent is extended or adjusted under 35 U.S.C. 154(b) by 626 days.

This patent is subject to a terminal disclaimer.

(21) Appl. No.: 17/079,905

(22) Filed: Oct. 26, 2020

(65) Prior Publication Data

US 2021/0042690 A1 Feb. 11, 2021

Related U.S. Application Data

(63) Continuation of application No. 15/615,369, filed on Jun. 6, 2017, now Pat. No. 10,817,834, which is a
(Continued)

(51) Int. Cl.
*G06Q 10/087* (2023.01)
*G16H 20/10* (2018.01)
(Continued)

(52) U.S. Cl.
CPC .......... *G06Q 10/087* (2013.01); *G06Q 50/22* (2013.01); *G16H 20/10* (2018.01); *G16H 20/60* (2018.01)

(58) Field of Classification Search
CPC ...... G06Q 10/087; G06Q 50/22; G16H 20/10; G16H 20/60
See application file for complete search history.

(56) References Cited

U.S. PATENT DOCUMENTS 3,953,769 A * 4/1976 Sopko ................ G07C 9/00674
340/5.31
4,148,092 A * 4/1979 Martin ............... G07C 9/00904
70/268

(Continued)

FOREIGN PATENT DOCUMENTS

EP 0510686 B1 7/1997
EP 1650536 A2 4/2006
(Continued)

OTHER PUBLICATIONS

Definition of "On" as "In Contact or Connection with the Surface of" as defined in World English Dictionary, 1998, Williams Collins Sons & Co.
(Continued)

*Primary Examiner* — Nathaniel T Woodward
*Assistant Examiner* — Philip L Cotey
(74) *Attorney, Agent, or Firm* — McGarry Bair PC

(57) ABSTRACT

A refrigerator is provided with a container for storing a substance and that has a sensing and reporting system configured to determine an amount of the substance within the container. The sensing and reporting system includes a sensor configured to sense the amount of the substance, a transmitter, and a processor in communication with the sensor and the transmitter.

19 Claims, 14 Drawing Sheets

Related U.S. Application Data continuation of application No. 12/256,502, filed on Oct. 23, 2008, now abandoned.

(51) Int. Cl.
  *G16H 20/60* (2018.01)
  *G06Q 50/22* (2018.01)

(56) References Cited

U.S. PATENT DOCUMENTS

| | | | | |
|---|---|---|---|---|
| 4,605,297 A * | 8/1986 | Livingston | G03D 9/00 | 396/587 |
| 4,684,945 A * | 8/1987 | Sanderford, Jr. | G07C 9/00912 | 70/278.1 |
| 4,939,705 A * | 7/1990 | Hamilton | A61J 7/0436 | 368/10 |
| 4,998,824 A * | 3/1991 | Littlejohn | G01N 21/31 | 209/582 |
| 5,008,661 A * | 4/1991 | Raj | G07C 9/28 | 340/10.33 |
| 5,014,798 A * | 5/1991 | Glynn | G01G 19/14 | 222/23 |
| 5,153,561 A * | 10/1992 | Johnson | G08B 13/149 | 70/278.1 |
| 5,187,744 A * | 2/1993 | Richter | F16M 11/041 | 379/426 |
| 5,305,381 A * | 4/1994 | Wang | B60R 11/0241 | 379/426 |
| 5,448,220 A * | 9/1995 | Levy | G08B 13/2434 | 340/505 |
| 5,457,745 A * | 10/1995 | Wang | B60R 11/0241 | 379/426 |
| 5,491,333 A * | 2/1996 | Skell | G01F 23/2921 | 250/559.31 |
| 5,544,572 A * | 8/1996 | Garmendia | A23N 1/003 | 99/489 |
| 5,586,085 A * | 12/1996 | Lichte | G01F 25/20 | 367/908 |
| 5,710,551 A * | 1/1998 | Ridgeway | A61J 7/0084 | 128/920 |
| 5,836,563 A * | 11/1998 | Hsin-Yung | B60R 11/0241 | 379/426 |
| 5,852,590 A * | 12/1998 | de la Huerga | G06K 19/07762 | 368/10 |
| 5,905,653 A * | 5/1999 | Higham | G07F 17/0092 | 700/242 |
| 5,983,198 A * | 11/1999 | Mowery | G06Q 20/203 | 705/16 |
| 6,137,413 A * | 10/2000 | Ryan, Jr. | B65D 55/028 | 340/572.1 |
| 6,243,613 B1 * | 6/2001 | Desiraju | G06Q 10/0875 | 700/106 |
| 6,259,654 B1 * | 7/2001 | de la Huerga | A61J 7/0481 | 368/10 |
| 6,271,753 B1 * | 8/2001 | Shukla | B65D 55/028 | 340/571 |
| 6,341,271 B1 * | 1/2002 | Salvo | G06Q 10/087 | 705/28 |
| 6,382,416 B1 * | 5/2002 | Gainey | A61J 1/1437 | 206/317 |
| 6,529,446 B1 * | 3/2003 | de la Huerga | A61J 7/0481 | 368/10 |
| 6,634,279 B2 * | 10/2003 | D'Antonio | A47J 31/56 | 99/275 |
| 6,707,381 B1 * | 3/2004 | Maloney | G07F 9/026 | 340/568.1 |
| 6,735,497 B2 * | 5/2004 | Wallace | G07F 9/002 | 700/231 |
| 6,751,730 B1 * | 6/2004 | Walker | G07F 17/3218 | 713/161 |
| 6,779,024 B2 * | 8/2004 | DeLaHuerga | G16H 10/65 | 709/217 |
| 6,785,567 B2 * | 8/2004 | Kato | H04B 1/3877 | 379/433.11 |
| 6,859,745 B2 * | 2/2005 | Carr | B65D 51/245 | 702/81 |
| 6,879,876 B2 * | 4/2005 | O'Dougherty | B67D 7/348 | 700/285 |
| 6,888,940 B1 * | 5/2005 | Deppen | B60R 11/0241 | 379/454 |
| 6,966,533 B1 * | 11/2005 | Kalis | F16M 13/022 | 248/316.4 |
| 6,996,538 B2 * | 2/2006 | Lucas | G06Q 30/0613 | 705/28 |
| 7,017,807 B2 * | 3/2006 | Kipp | B65D 51/24 | 340/568.1 |
| 7,061,380 B1 * | 6/2006 | Orlando | G08B 21/18 | 374/E1.004 |
| 7,080,812 B2 * | 7/2006 | Wadsworth | B60R 11/02 | 248/316.4 |
| 7,130,814 B1 * | 10/2006 | Szabo | G06Q 30/0201 | 705/7.29 |
| 7,158,092 B2 * | 1/2007 | Shen | H04M 1/04 | 343/878 |
| 7,190,750 B2 * | 3/2007 | Teague | H04B 1/7117 | 375/E1.032 |
| 7,192,108 B2 * | 3/2007 | Lyman | B41J 2/17509 | 347/7 |
| 7,224,273 B2 * | 5/2007 | Forster | G01F 23/2966 | 340/572.1 |
| 7,292,993 B2 * | 11/2007 | Uzzo | G06Q 20/203 | 705/28 |
| 7,342,501 B2 * | 3/2008 | Abbott | B65D 41/045 | 340/568.1 |
| 7,366,675 B1 * | 4/2008 | Walker | G06Q 10/109 | 705/2 |
| 7,388,506 B2 * | 6/2008 | Abbott | B65D 41/045 | 340/572.1 |
| 7,479,887 B2 * | 1/2009 | Meyer | B65D 41/3423 | 340/572.1 |
| 7,484,388 B2 * | 2/2009 | Crisp, III | G06Q 10/087 | 68/17 R |
| 7,486,188 B2 * | 2/2009 | Van Alstyne | G06Q 10/087 | 340/505 |
| 7,495,561 B2 * | 2/2009 | Bodin | G06Q 10/08 | 340/572.1 |
| 7,525,421 B2 * | 4/2009 | Levesque | G08B 21/12 | 340/517 |
| 7,663,497 B2 * | 2/2010 | Chishima | G01F 23/284 | 340/613 |
| 7,673,464 B2 * | 3/2010 | Bodin | G06Q 10/08 | 347/141 |
| 7,693,603 B2 * | 4/2010 | Higham | G07C 9/00912 | 700/242 |
| 7,696,869 B2 * | 4/2010 | Brown | G06Q 10/06 | 340/517 |
| 7,715,277 B2 * | 5/2010 | de la Huerga | G06K 19/07762 | 340/572.1 |
| 7,731,308 B1 * | 6/2010 | Riemer | E05B 63/24 | 312/307 |
| 7,761,319 B2 * | 7/2010 | Gil | G06Q 10/0631 | 705/7.38 |
| 7,766,242 B2 * | 8/2010 | Lunak | G16H 20/13 | 235/383 |
| 7,772,981 B1 * | 8/2010 | Lambert | B65D 47/088 | 340/539.1 |
| 7,801,745 B2 * | 9/2010 | Walker | A61J 7/0481 | 221/9 |
| 7,821,404 B2 * | 10/2010 | Walker | A61J 7/04 | 463/43 |
| 7,844,509 B2 * | 11/2010 | Bodin | G06Q 10/087 | 340/572.1 |
| 7,887,755 B2 * | 2/2011 | Mingerink | B65D 23/00 | 340/572.1 |
| 7,894,938 B1 * | 2/2011 | Arora | G07F 9/026 | 705/28 |
| 7,930,060 B2 * | 4/2011 | Yuyama | G07F 17/0092 | 700/214 |

(56) References Cited

U.S. PATENT DOCUMENTS

| | | | | |
|---|---|---|---|---|
| 7,933,733 B2* | 4/2011 | Ashrafzadeh | G01F 23/2928 | 702/116 |
| 7,937,289 B2* | 5/2011 | Bodin | G06Q 20/203 | 705/28 |
| 7,961,104 B2* | 6/2011 | Bodin | G06Q 50/28 | 340/572.1 |
| 7,978,564 B2* | 7/2011 | De La Huerga | A61M 5/16827 | 700/242 |
| 7,991,507 B2* | 8/2011 | Liff | G06Q 10/087 | 221/13 |
| 7,999,679 B2* | 8/2011 | Van Alstyne | G07G 1/0045 | 340/505 |
| 8,006,903 B2* | 8/2011 | Braun | G06Q 10/087 | 235/383 |
| 8,032,430 B2* | 10/2011 | Bodin | G06Q 10/087 | 705/28 |
| 8,040,244 B2* | 10/2011 | Bauchot | H04Q 9/00 | 340/568.1 |
| 8,055,509 B1* | 11/2011 | Walker | G06Q 10/087 | 600/300 |
| 8,069,056 B2* | 11/2011 | Walker | G06Q 30/0224 | 705/28 |
| 8,120,484 B2* | 2/2012 | Chisholm | G06K 19/07749 | 340/572.1 |
| 8,477,029 B2* | 7/2013 | Ashrafzadeh | G06Q 10/087 | 340/625 |
| 10,817,834 B2* | 10/2020 | McCoy | G16H 20/10 | |
| 2002/0027507 A1* | 3/2002 | Yarin | G16H 20/13 | 705/2 |
| 2002/0116509 A1* | 8/2002 | DeLaHuerga | A61J 7/0084 | 713/176 |
| 2002/0183883 A1* | 12/2002 | Carr | B65D 55/028 | 340/584 |
| 2003/0099158 A1* | 5/2003 | De la Huerga | A61J 1/1437 | 368/10 |
| 2003/0152673 A1* | 8/2003 | Tarlow | B65D 81/18 | 426/118 |
| 2003/0174554 A1* | 9/2003 | Dunstone | G07C 9/28 | 365/200 |
| 2003/0179073 A1* | 9/2003 | Ghazarian | E05B 47/00 | 340/5.6 |
| 2003/0216831 A1* | 11/2003 | Hart | G16H 15/00 | 700/235 |
| 2004/0030532 A1* | 2/2004 | Boldt | G01D 9/005 | 702/187 |
| 2004/0100380 A1* | 5/2004 | Lindsay | G06K 19/0717 | 340/572.1 |
| 2004/0103144 A1* | 5/2004 | Sallam | H04L 67/12 | 709/236 |
| 2004/0124988 A1* | 7/2004 | Leonard | B05B 11/0054 | 340/612 |
| 2004/0160304 A1* | 8/2004 | Mosgrove | G07C 9/27 | 713/193 |
| 2004/0254862 A1* | 12/2004 | Luo | G06Q 10/087 | 705/28 |
| 2005/0051624 A1* | 3/2005 | Kipp | B65D 55/02 | 235/385 |
| 2005/0146419 A1* | 7/2005 | Porter | A24F 15/005 | 340/5.28 |
| 2005/0258961 A1* | 11/2005 | Kimball | G06Q 20/203 | 340/572.1 |
| 2006/0012481 A1* | 1/2006 | Rajapakse | G06Q 10/00 | 340/572.1 |
| 2006/0015414 A1* | 1/2006 | Congram | G06Q 10/087 | 705/28 |
| 2006/0019135 A1* | 1/2006 | Curello | H01M 8/04089 | 429/442 |
| 2006/0049948 A1* | 3/2006 | Chen | G06K 19/073 | 235/492 |
| 2006/0064257 A1* | 3/2006 | Pennington | G01F 22/02 | 702/50 |
| 2006/0119484 A1* | 6/2006 | Chishima | G01F 23/2845 | 340/539.1 |
| 2006/0285441 A1* | 12/2006 | Walker | A61J 7/04 | 368/10 |
| 2007/0030143 A1* | 2/2007 | Benson | G07C 9/257 | 340/508 |
| 2007/0097792 A1* | 5/2007 | Burrows | G16H 10/60 | 368/10 |
| 2007/0152048 A1* | 7/2007 | Jung | G06Q 20/203 | 235/383 |
| 2007/0192715 A1* | 8/2007 | Kataria | G16H 10/40 | 705/28 |
| 2007/0204691 A1* | 9/2007 | Bogner | A61B 5/6892 | 73/432.1 |
| 2007/0227913 A1* | 10/2007 | Shoenfeld | E05B 63/24 | 206/1.5 |
| 2008/0041947 A1* | 2/2008 | Hollister | G06Q 10/08 | 340/572.1 |
| 2008/0047282 A1* | 2/2008 | Bodin | G06Q 10/087 | 62/129 |
| 2008/0052001 A1* | 2/2008 | Bodin | G16H 20/60 | 708/133 |
| 2008/0052200 A1* | 2/2008 | Bodin | G06Q 10/0875 | 705/28 |
| 2008/0052201 A1* | 2/2008 | Bodin | G06Q 10/087 | 705/28 |
| 2008/0052202 A1* | 2/2008 | Bodin | G06Q 10/087 | 705/28 |
| 2008/0059338 A1* | 3/2008 | Hubbard | G06Q 10/087 | 705/28 |
| 2008/0164984 A1* | 7/2008 | Sheffer | H04K 3/88 | 340/426.13 |
| 2008/0173668 A1* | 7/2008 | Bloechlinger | G01F 13/00 | 222/1 |
| 2008/0184719 A1* | 8/2008 | Lowenstein | G16Z 99/00 | 62/127 |
| 2008/0186136 A1* | 8/2008 | Raphaeli | G01S 5/14 | 340/10.1 |
| 2008/0211674 A1* | 9/2008 | Gibson | G06Q 10/08 | 705/28 |
| 2008/0303663 A1* | 12/2008 | Smith | G08B 13/20 | 340/550 |
| 2009/0277199 A1* | 11/2009 | Manas | F25D 29/00 | 62/441 |
| 2009/0317311 A1* | 12/2009 | Cocking | D06F 33/37 | 422/261 |
| 2010/0007464 A1* | 1/2010 | McTigue | G06Q 10/087 | 340/10.1 |
| 2010/0106515 A1* | 4/2010 | McCoy | G16H 20/10 | 705/28 |
| 2010/0117797 A1* | 5/2010 | Bauchot | H04Q 9/00 | 220/212 |
| 2010/0161140 A1* | 6/2010 | Doglioni Majer | A47J 31/402 | 222/129 |
| 2010/0241277 A1* | 9/2010 | Humphrey | G01F 23/00 | 700/282 |
| 2010/0253519 A1* | 10/2010 | Brackmann | B60P 3/03 | 340/572.1 |
| 2010/0326283 A1* | 12/2010 | Evers | A47J 31/56 | 222/541.6 |
| 2021/0042690 A1* | 2/2021 | McCoy | G06Q 10/087 | |

FOREIGN PATENT DOCUMENTS

| | | |
|---|---|---|
| EP | 1777467 A1 | 4/2007 |
| EP | 1810598 A1 | 7/2007 |
| JP | 7218320 A | 8/1995 |
| JP | 2001264146 A | 9/2001 |
| JP | 2001264147 A | 9/2001 |
| JP | 2002291844 A | 10/2002 |
| JP | 2004283248 A | 10/2004 |
| JP | 2008216165 A | 9/2008 |
| SK | 284643 B6 | 8/2005 |
| WO | 99/01971 A1 | 1/1999 |
| WO | 02100728 A2 | 12/2002 |

(56) References Cited

FOREIGN PATENT DOCUMENTS

| WO | 03101022 A2 | 12/2003 |
| WO | 2005093377 A2 | 10/2005 |
| WO | 2006/126818 A1 | 11/2006 |

OTHER PUBLICATIONS

Definition of "Appliance" Retrieved from Merrium-Webster's Medical Dictionary, 2007.
Definition of "Ingredient" Retrieved from Collins English Dictionary, Complete & Unabridged 10th Edition, 1979.
Definition of "Foodstuff" Retrieved from Collins English Dictionary, William Collins & Co., 2007.

* cited by examiner

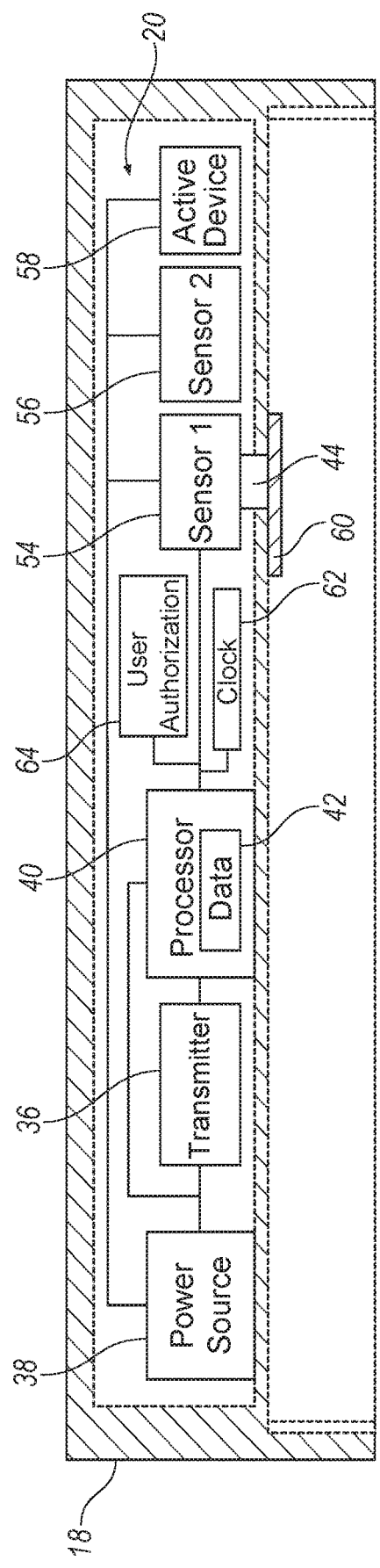
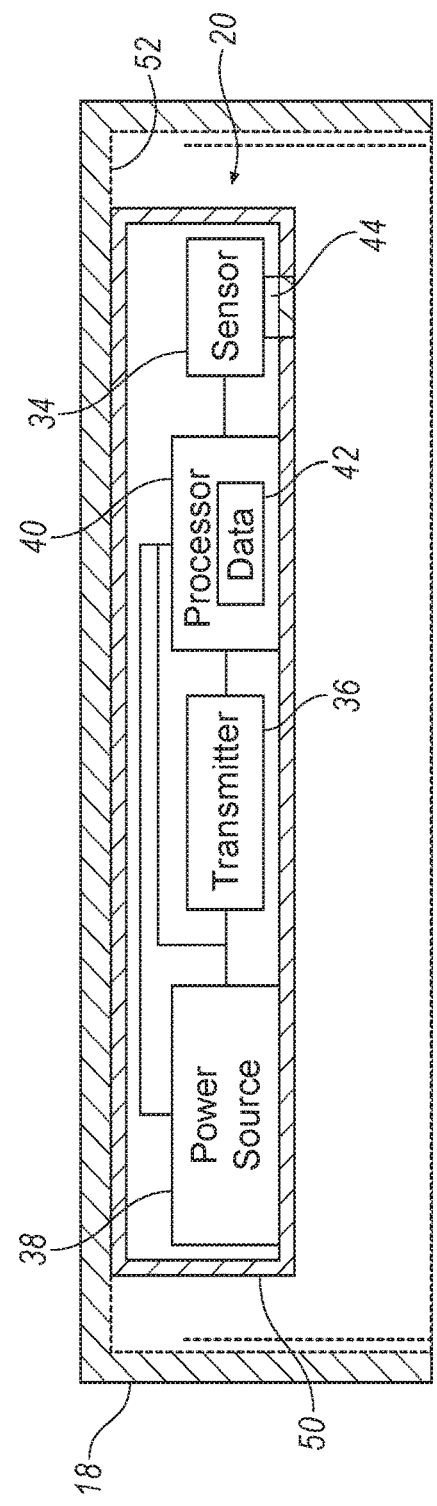
Figure 4
Figure 5

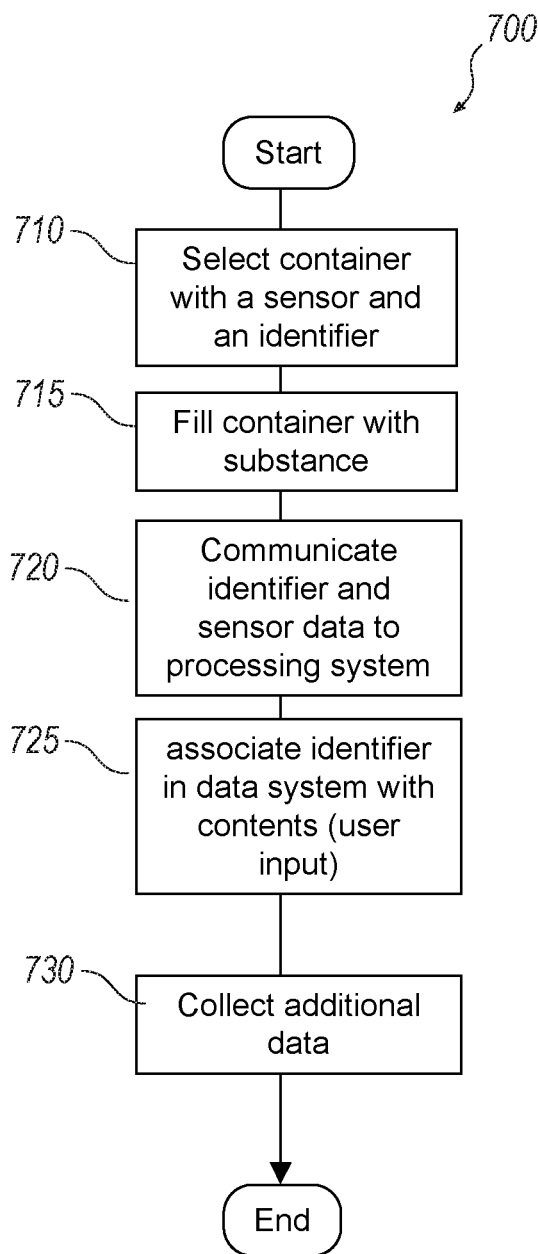
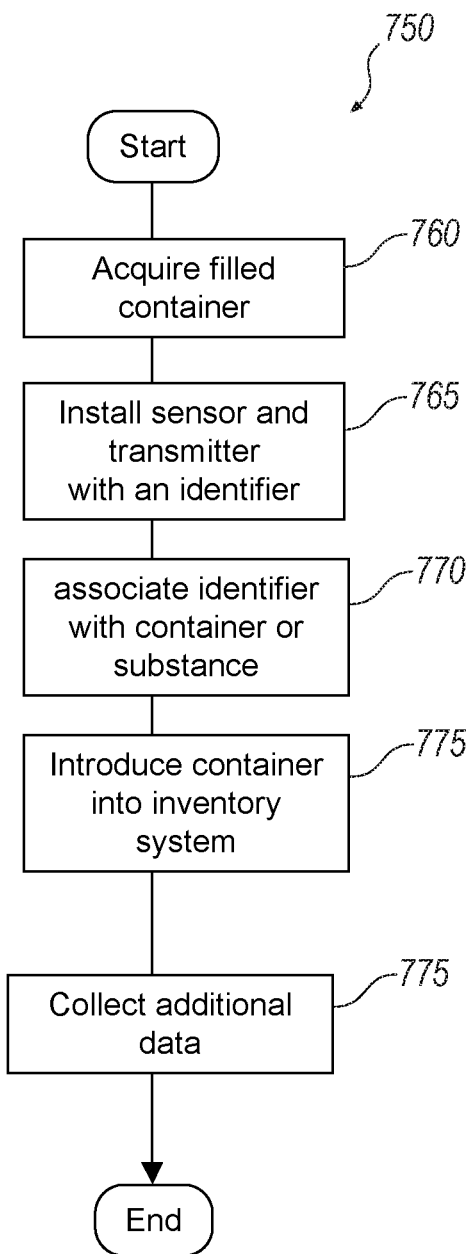
*Figure 12*  *Figure 13*

SYSTEM WITH REFRIGERATOR AND SELF-REPORTING CONTAINER

CROSS-REFERENCE TO RELATED APPLICATION(S)

This application is a continuation of U.S. patent application Ser. No. 15/615,369, filed Jun. 6, 2017, now U.S. Pat. No. 10,817,834, issued Oct. 27, 2020, which is a continuation of U.S. patent application Ser. No. 12/256,502, filed Oct. 23, 2008, now abandoned, both of which are incorporated herein by reference in their entirety.

TECHNICAL FIELD

The invention relates to a method of inventory management using container-based sensors for determining an attribute of a substance and for selectively introducing and activating self-reporting containers for participating in an inventory management system.

BACKGROUND

There are numerous containers of various types configured to store all matter of substances. However, determining the amount of the substance stored in the container, which is often useful to know, may be difficult to ascertain. Containers that can self-report the amount of their contents could save significant amounts of manual measuring or guesswork. Additionally, many secondary applications may be available from having a system of containers that self-report the amounts of their contents.

In a kitchen environment, knowing the amount of container contents, such as food, can facilitate more informed food consumption and food purchase decisions. In a household kitchen, particularly when children have access to the kitchen, it may be difficult to regulate or keep track of the removal of food substances from containers. In a commercial kitchen including multiple food preparers rapidly preparing dishes in a stressful environment, the task of tracking the amounts of food substances in numerous containers can be even more challenging.

In a laboratory environment, chemicals, and the like, may require detailed usage tracking. For instance, the substances may be expensive or hazardous. Such usage tracking may require careful removal and measuring of the substance and a recordation of the amount removed in a logbook.

Without accurate inventory determinations, maintaining inventory levels may be an ad hoc process. In one approach, inventory trends may be learned over time. However, any identified trends may be upset by unexpected usage. Accordingly, a device to accurately report the amount of a substance stored in a container at any given time may be useful in an inventory system.

SUMMARY

According to one aspect of the invention, a system includes a refrigerator, a container within the refrigerator for storing a substance and having a sensing and reporting system configured to determine an amount of substance within the container. The sensing and reporting system has a sensor configured to sense the amount of substance in the container, a transmitter in communication with a remote device, and a processor in communication with the sensor and the transmitter. Upon moving the container, the processor is configured to activate the sensor to sense the amount of substance in the container and provide an indication of the sensed amount of substance in the container to the processor. The processor is also configured to activate the transmitter to transmit the indication of the amount of substance to the remote device.

According to another aspect of the invention, a system includes a refrigerator, a container within the refrigerator for storing a substance and having a sensing and reporting system configured to determine an amount of the substance within the container. The sensing and reporting system has a sensor configured to sense the amount of the substance, a transmitter, a processor in communication with the sensor and the transmitter, and a control unit in communication with the transmitter of the sensing and reporting system, and comprising a visual display and a control interface.

BRIEF DESCRIPTION OF THE DRAWINGS

In the drawings:

FIG. 4 is a partially schematic side, cut away view of an alternative exemplary lid based amount sensor including additional modules.

FIG. 5 is a partially schematic side, cut away view of an exemplary lid based amount sensor included as a removable component.

FIG. 12 is a flow chart depicting exemplary steps in activating a container filled with the substance at the time of introduction into the use environment.

FIG. 13 is a flow chart depicting exemplary steps in activating a container to which a transmitter is added at the use environment.

DETAILED DESCRIPTION

Figure 1:
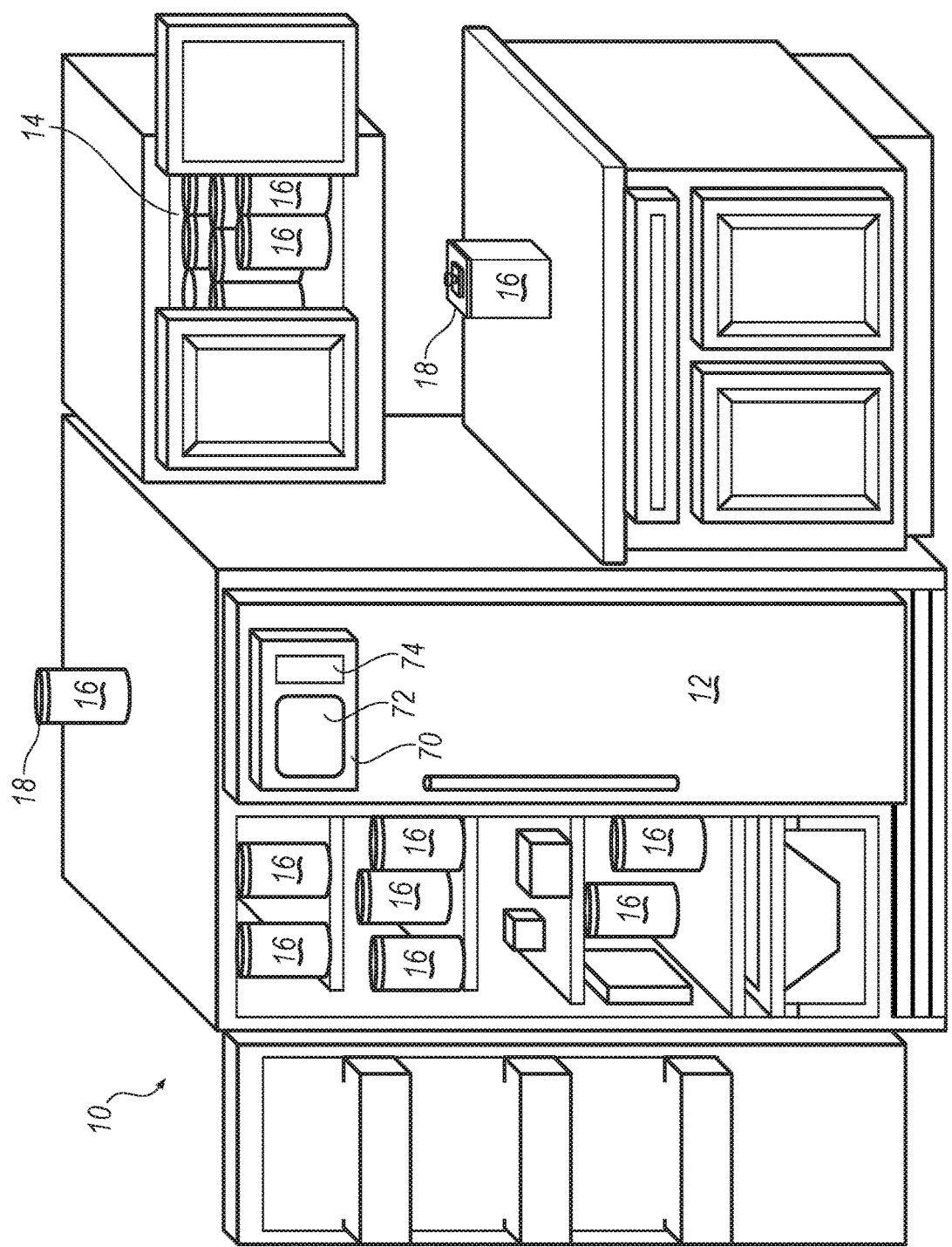
FIG. 1 is a perspective partial view of a kitchen including a refrigerator and cabinets each holding numerous containers.

Container based sensors that are configured to provide an indication of the amount of a substance may facilitate inventory management procedures. Accordingly, exemplary sensing devices are described immediately below followed by descriptions of inventory management procedures.

As used herein, a substance is any useful material that can be stored in a container. A consumable substance is a substance that may be stored in varying amounts in containers and may be partially dispensed or removed from the container over a period of time. An attribute of a substance is any information about a substance, including measurable and non-measurable information about the substance that can be stored for later retrieval, including but not limited to its physical or chemical properties, its impact upon its environment, and its amount.

Non-measurable attributes are attributes about the substance that may be stored with the substance or with the container of the substance, whether the attributes would or would not have been measurable by an appropriate sensor. Examples of non-measurable attributes include quantity of consumable pieces, quantity by volume or by weight, date of manufacture, manufacturer, data about its transit from manufacturer, distributor, market, and consumer, data about the temperature during transit, nutritional information like calories, fat grams, daily allowance of essential vitamins and minerals, a list of medical conditions under which a consumable should not be consumed, data about the relationship between the Consumable Meta Data and known diets, known medical conditions, and known reactions to known medications, and the like.

Attributes may be determined by a single measurement or may be derived from multiple measurements, such as measurements of multiple types, measurements taken at multiple locations or measurements taken at multiple times and may reflect static conditions, such as temperature or quantity, or dynamic conditions such as change, rate of change, or change in rate of change.

Amount attributes are attributes directly reflecting the amount of the substance available for future use including weight, volume, mass, height, and count. An attribute indicative of the amount are attributes that may be used or processed to infer or calculate the amount of substance, such as the vapor pressure in a container, the light transmissivity or electrical inductance, capacitance, resistance, reactance, or impedance of the substance. An attribute of the environment is any characteristic of the environment inside of the container, the environment outside of the container, or of the container itself.

As used herein, information or data includes any stored information, such as genealogical and life cycle information, relating to the substance, the container, the manufacturer, the environment, the user or users. Information may be measurable or non-measurable, event based, historical, or identifier information.

Since there can be a plurality of containers, each with a substance, there may need to be a unique identifier identifying each container or each substance that may be paired with an attribute measurement of a substance so that the value of the measurement can be uniquely identified per its meaning at a later time and by subsequent intelligent processes. Such identifier may be associated with the substance, the container, the sensor, or the transmitter and such association may occur at the time of creation or assembly of the components, the time of first adding substance to the container, or the time of introducing the container to a system using a plurality of containers. The identifier may also be dynamically generated, for example, from one or more measurable and non-measurable attributes.

Similarly, since there may be a plurality of attributes applicable to a substance, attributes may need to be uniquely identifiable so that when a collection of attributes each having a value is either stored or transmitted, each respective value is paired with its attribute identifier so that the value can be uniquely identified per its meaning at a later time and by a subsequent intelligent process. In the simplest case, where there is only an amount attribute, the system may assume that all values are amount values with an inherent attribute identifier with the meaning of amount.

A container of substance is any container capable of temporarily holding an amount of substance.

A lid is a feature of any container which may be opened to permit or improve access to the substance in the container. A dispenser is any feature of a container which permits or drives the active or passive filling of substance into the container or which permits or drives the active dispensing of substance from the container. A main body of a container is any portion of the container which is not a lid or dispenser. A portable container is a container that is intended to be periodically manually moved within a use environment during its lifetime.

A sensor is any active or passive device capable of obtaining information in a form which may be either actively or passively communicated to another device for use by the other device. A communication of information is the delivery of information from a first device to a second device either by the active transmission from the first device to the second device or by the reading of the second device by the first device. A transmitter is any device which wirelessly communicates information to other devices using any form of active or passive transmission including optical or electromagnetic waves.

A triggering event is an event used as an input by a system to begin a process. An access device of a container is any feature of a container that permits access to the substance, including any lid or dispenser. A triggering event relating to a container may be an access event, as defined herein, or alternatively any other physical or virtual event relating to the container or its contents, including expiration, pending or projected expiration, scheduled or projected use in a recipe, scheduled or projected consumption, such as for use in recipe, Examples of triggering events are execution of a firmware or software, opening a container, receiving a network message, a clock tick, a period of a function like a sine wave, and the like.

An access event relating to a container of substance is any event indicative of accessing the substance in a container such as an opening, closing, dispensing or filling event.

A local event, device, process or step is an event, device, process or step existing or occurring in or about the container.

A remote event, device, process or step is an event, device, process or step existing or occurring remote from the container.

A notification is specific information derived from a system which is a value to a user or to an observing computer program on a remote device. A notification event is an event resulting in the immediate availability of information to a user or the delivery of information to a user, such as audible announcement, a visible display on a user interface, a communication to phone or other portable consumer electronic device, or a notification message either broadcast on at least one computer network or directed to at least one computer containing a software component configured to receive the notification.

As used herein, a container system member is any identifiable physical component or subsystem of a container and its contents, including the container, the lid of a container, a sensor, a transmitter, a dataset affixed directly or indirectly to the container, and a substance within the container. Container system data is any data or attribute of a container system member.

Power and energy include any form of power or energy usable by a device for performing an operation and includes electrical, mechanical and chemical power. A power generator is any device capable of generating a usable form of power or energy. A power converter is any device capable of converting one form of power to another such as converting chemical power to electrical power, or converting AC electrical power to DC electrical power.

As used herein, inventory management includes any system, device or apparatus useful to support the acquisition, storage, use, disposal, and replenishment of consumable substances in a storage and use environment.

Association is the creation of a physical or virtual relationship between two physical or virtual elements, such as the physical connection between two physical components or the virtual association in a database of an attribute of a physical element with another attribute or with an identifier.

Activation is any step in the preparation of any physical or virtual component for participation in an inventory system. Activation of a container includes, for example, the preparation of a container to be self reporting for use in an inventory system or the initiation of communication between the container and a data processing system. Activation of a data processing system for an inventory system includes, for example, the initiation communication between the data processing system and a container of substance or the creation of a record associated with the container or the substance in the data processing system. Activation includes the association of a container with a substance or the association of either with an identifier, a notification trigger rule or a user ID. Activation may include local process steps at a container, local process steps at a data processing system remote from the container, steps involving communication with data systems remote from both the container and the data processing system, or combinations thereof.

Referring now to the drawings, preferred embodiments of the present invention are shown in detail. Although the drawings represent embodiments of the present invention, the drawings are not necessarily to scale and certain features may be exaggerated to better illustrate and explain the present invention. The embodiments set forth herein are not intended to be exhaustive or otherwise limit the invention to the precise forms disclosed in the following detailed description.

Figure 2:
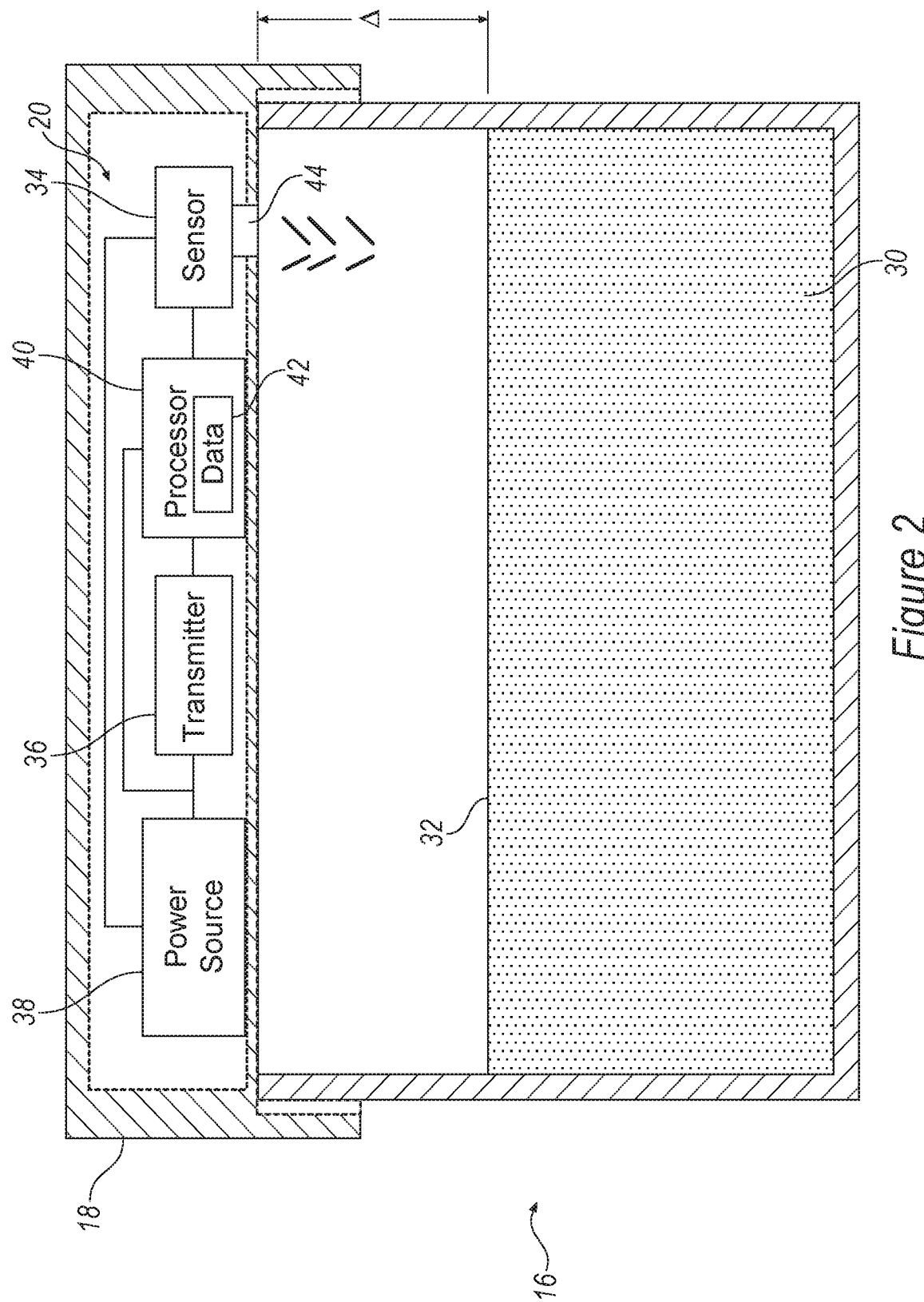
FIG. 2 is a partially schematic side, cut away view of a container including an exemplary lid based device including an amount sensor.
Figure 2A:
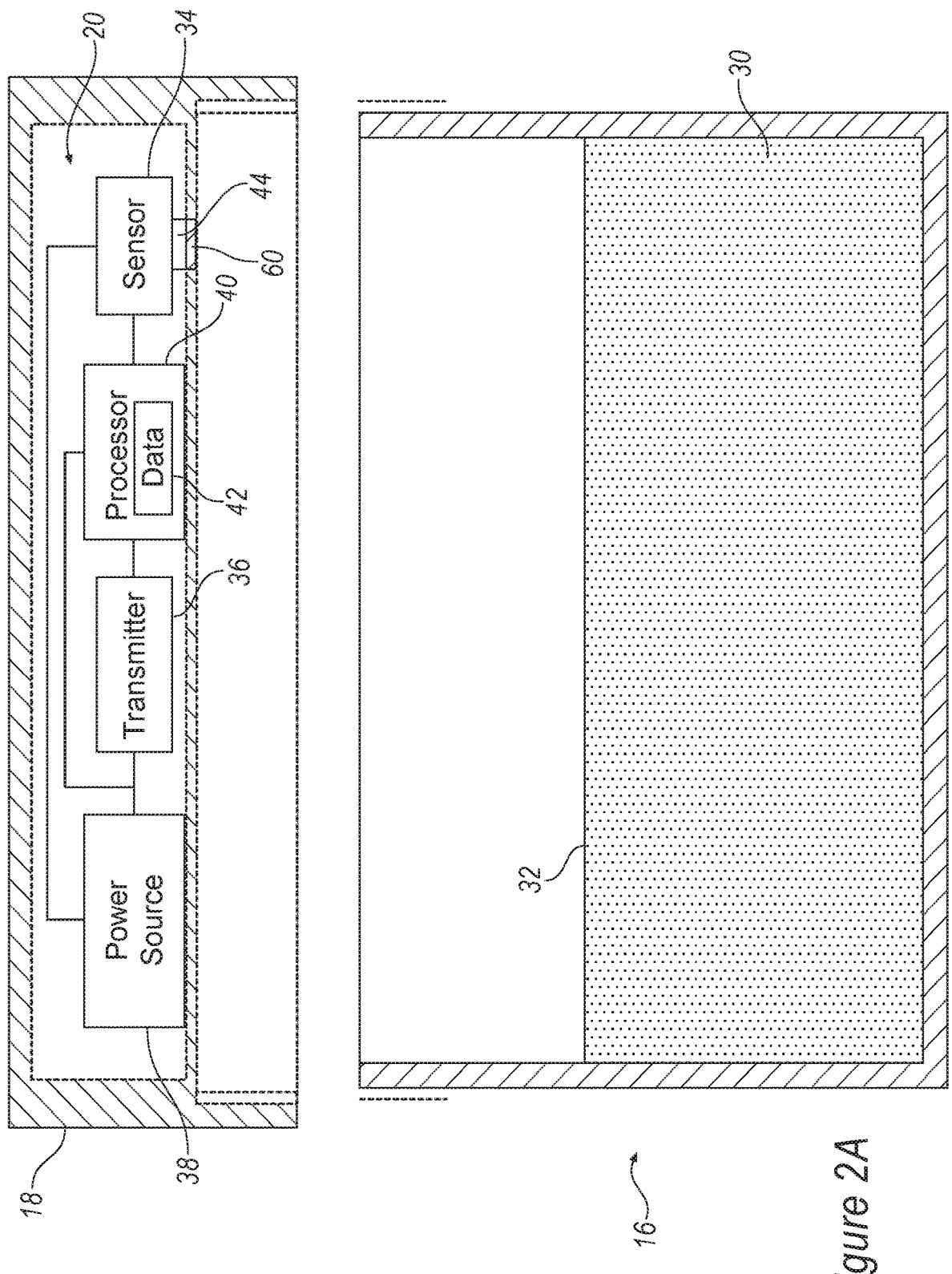
FIG. 2A is a partially schematic side, cut away, exploded view of the container of FIG. 2 including an exemplary lid based device including an amount sensor showing the lid removed from the container.

Referring now to FIGS. 1, 2, and 2A, a storage and consumption environment such as a kitchen 10, may include a refrigerator 12 and cabinetry 14 that may each hold a plurality of containers 16. The exemplary kitchen 10 could have additional cupboards and pantries holding additional containers 16. Containers 16 may be enclosed in a storage unit, such as a refrigerator 12 or in the cabinetry 14, or may be in an unconfined location, such as the depiction of a container 16 on top of refrigerator 12. Containers 16 generally include a lid 18 for enclosing a substance 30 being contained. The lid 18 may also provide a sensing and reporting system 20. Sensing and reporting system 20 may be configured to determine an attribute of the substance such as the amount of substance 30 that is contained in container 16. Moreover, in an environment, such as kitchen 10 with multiple containers 16, each container 16 may independently determine the amount of substance 30 contained therein, for example, through sensing and reporting device 20 disposed in a respective lid 18 of container 16.

The manufacture of containers 16 which can self-report data about their contents is contemplated. Specific embodiments of self-reporting containers 16, as well as some additional related components, methods and features will now be described. Other examples of self-reporting containers are described in the following related patent publications: U.S. Patent Application Publication No. 2010/0101317, entitled "LID BASED AMOUNT SENSOR", U.S. Pat. No. 8,477,029, entitled "MODULAR ATTRIBUTE SENSING DEVICE," U.S. Patent Application Publication No. 2010/0106624, entitled "METHOD OF INVENTORY MANAGEMENT," U.S. Pat. No. 7,933,733, entitled "ATTRIBUTE SENSING PROCESSES," U.S. Patent Application Publication No. 2010/0106626, entitled "SYSTEM AND METHOD FOR TRACKING INVENTORY HISTORY," U.S. Patent Application Publication No. 2010/0106625, entitled "INVENTORY COMPONENT ACTIVATION," U.S. Patent Application Publication No. 2010/0106521, entitled "CONSUMABLES INVENTORY MANAGEMENT METHOD," now U.S. Pat. No. 9,691,114, and U.S. Patent Application Publication No. 2010/0102930, entitled "INTRODUCTION OF A SELF-REPORTING PORTABLE CONTAINER INTO AN INVENTORY SYSTEM," each of which is incorporated herein by reference in its entirety.

In general, a container 16 may be manufactured and configured with sensing and reporting system 20.

The sensing and reporting system may include analog or digital componentry which is able to determine information about a substance 30 or information associated with a substance like amount, temperature, and the like. In particular, as shown in FIGS. 2 and 2A a sensing and reporting system 20 may include sensing apparatus, such as a sensor 34, and reporting apparatus, such as a transmitter 36.

It should be noted that the sensing apparatus may be provided with the main body of a container 16 or with the lid 18, or with a dispensing apparatus, not shown. The container 16 may be filled at the facility where it is manufactured or where it is first associated with the sensing and reporting apparatus 20 or it may be shipped to another facility for filling. At some point during the manufacturing or distribution process, the container 16 or the container's sensing and reporting system 20 is associated with at least one identifier. The identifier may be a globally unique identifier like a UUID, a bar code, a serial number, a substance identifier, or a multiplicity of identifiers which together characterize at least one of the container, the substance, and attributes thereof. If the container has compartments for more than one substance, then an identifier may be associated with each compartment or with the substances in each compartment. Once the container 16, the substance 30, and the sensing and reporting apparatus 20 are united, the container is configured to determine and selectively report the identifiers and the information.

The reporting and sensing system 20 is configured with rules which dictate the conditions on which the reporting apparatus and or the sensing apparatus are active. When active, the reporting apparatus transmits the information to an information destination. When active, the sensing apparatus determines information about a substance 30.

Sensing and reporting may be continuous or event (trigger) based. If continuous, the sensor continuously senses information about the substance and the reporting apparatus continuously transmits information to an information destination. If triggered, the sensor senses when the triggering rule is activated.

An exemplary triggering rule may be an access event as defined above. The reporting apparatus may use the same triggering rule, a different triggering rule, or may be triggered by another electrical mechanism like a digital input signal or an analog comparator circuit. Generally, when information about a substance is reported, it is reported with other information where the other information is the at least one identifier.

Referring again to FIGS. 2 and 2A, in addition to the sensing apparatus, such as a sensor 34, and reporting apparatus, such as a transmitter 36 the sensing and reporting system 20, may include a power source 38, a processor 40, and at least one element of data 42. Sensor 34, processor 40, and transmitter 36 may be communicatively coupled. In one exemplary approach, sensor 34, processor 40, and transmitter 36 may be separate physical elements coupled by communication wires. However, other exemplary approaches may include one or more of sensor 34, processor 40, transmitter 36, and power source 38 as a single physical element, such as an integrated circuit.

The reporting apparatus may be digital componentry able to communicate the information to an information destination. An information destination can be one which is external to the container or to an information storage device on the container or to a user interface on the container.

It is advantageous to make the sensing and reporting system 20 lightweight and compact in size. Transmitter and transceiver circuitry has been reduced, for example for RFID tags, to devices as small as a quarter square millimeter (0.25 mm$^2$) and as thin as five hundredths of a millimeter (0.05 mm). Such devices often include a radio-frequency circuit, an antenna, a processor, memory in the form of ROM, a current rectifying circuit and a power and/or synchronizing circuit, not shown in the drawing. For the amount sensing device 30, the processor 40 may be the same processor as is used by the transmitter 36 or may be a separate processor dedicated to the control of the sensor 34, the processing of the output of the sensor, and the communication with the transmitter. The data 42 may be ROM memory only or may include some form of writable memory.

Another exemplary approach using an integrated circuit may include Micro-Electro-Mechanical Systems (MEMS). MEMS, sometimes referred to as a system-on-a-chip could include the sensor 34, transmitter 36, power source 38, and processor 40 all on a single silicon chip. Additionally, other sensors 56 and active devices 58, both discussed below, could be included. The circuit based elements may be produced on the silicon chip using a traditional integrated circuit production method while the mechanical components may be produced by a micromachining or etching process. The small scale of a MEMS based device 20 may simplify the association of the device 20 with a container 16 and may reduce the power consumption of the components.

Power source 38 may provide electrical power to sensor 34, processor 40, and transmitter 36 through electrical transmission wires connected thereto.

Sensor 34 may include a sensing element and an output element to output a reading of the sensing element. In one exemplary approach, output element may simply be the communication wires connecting sensor 34 to processor 40 and transmitter 36. However, in other exemplary approaches, output element may format or adapt the reading of sensing element prior to output. For instance, the output of sensing element may require analog to digital conversion which may be provided by an analog to digital converter of output element.

Sensing element of sensor 34 may be configured to sense the distance ($\Delta$) between sensor 34 and a level 32 of substance 30. Sensor 34 of sensing and reporting device 20 may be attached to container 16 at a fixed reference point to provide consistent measurements of distance $\Delta$. In one exemplary approach, the reference point may be associated with lid 18. The reference point may represent the uppermost limit of level 32 such as a fill line of container 16. The amount of substance 30 may be determined based on distance $\Delta$ in relation to the physical shape of container 16.

Sensor 34 may utilize any of a number of sensing techniques. In one exemplary approach, sensor 34 employs an acoustic sensing technique. The acoustic sensing technique may include an ultrasonic generator, an ultrasonic receiver, a timer, and a processor. An ultrasonic pulse or plurality of pulses may be generated and directed at substance 30. The pulse may reflect off the surface 32 of substance 30 and be collected by the receiver. The timer may record the time between the generation and reception of the pulse. Distance $\Delta$ may be calculated based on the recorded time with respect to the speed of sound.

In another exemplary approach, sensor 34 may employ a capacitance sensing technique. The capacitance sensing technique provides a first capacitance plate and an electrical charge sensing element. Surface level 32 of substance 30 acts as a second capacitance plate. The first plate is charged to create an electrostatic field. The field is affected by distance $\Delta$ to surface level 32 in a manner that may be perceived by the sensing element. The sensed difference in the field may be used with a calculation or look-up table to determined distance $\Delta$.

In yet another exemplary approach, sensor 34 may employ an infrared (IR) sensing technique. The IR sensing technique may include an IR light source, an IR receiver, and a sensing element. Beams of IR light may be distributed from the light source at an angle. The beams reflected off of surface level 32 may be received by the IR receiver. Triangulation calculations may be used to determine distance $\Delta$. Infrared sensing may require two sensors 54, 56 such as the depiction in FIG. 4.

It is to be understood that the list of sensing technologies listed above is not an exhaustive list. Additional sensing technologies may also be suitable, e.g., inductive sensing, resistive sensing, evaporative gas sensing, image sensing, pressure sensing, float sensing or other mechanical sensing, strain gauge or force sensing, etc. An inductive sensor may pass a current through an inductive loop creating a magnetic field. A metal substance 30 in the presence of the magnetic field produced by the loop may effect the inductance of the loop. The change in inductance may be sensed by the inductive sensor to determine the proximity of the substance 30 to the sensor 54. A strain gauge sensor may measure deformation or strain of the container 16 cause by the substance 30. A foil pattern may be deformed by the strain thereby altering its resistive properties. The change in resistance may be measured and used to determine an indication of the amount of the substance 30. A float sensor may be used with a liquid substance 30. A float may ride against a vertically disposed set of contacts. The float may therefore complete a circuit at a set of contacts corresponding to the surface level 32 of the substance 30. A pressure or force based sensor such as a scale may be used to determine the weight of the substance 30. The weight may be used along with a known density of the substance in order to determine an indication of the amount of the substance 30.

An evaporative gas sensor may sense the concentration of the substance 30 that has evaporated into the air within the container. The concentration may vary based on the amount of the substance 30 in the container 16 and therefore may be used to determine an indication of the amount. Optical sensing may use a set of vertically arranged image sensors. The level 32 of the substance 30 may be determined based on the height of the last sensor to be obstructed by the substance 30. An image sensor may be used with a transparent container 16 in order to capture an image of the substance 30 including the surface level 32. An image processing device may use the image to determine an indication of the amount based on the surface level 32.

An aperture 44 may be provided in lid 18 to facilitate operation of sensor 34. In another exemplary approach, aperture 44 may be covered with a protective element 60. Protective element 60 may further be a lens for an IR or optical based sensor 34.

Accordingly, while sensor 34 may be provided by numerous sensing technologies, any particular sensor 34 may determine distance $\Delta$. In one exemplary approach, sensor 34 may output distance $\Delta$ to transmitter 36. In such an approach, a control unit 70, discussed below, may receive the transmitted distance $\Delta$ and calculate the amount of substance 30 based on distance $\Delta$. In another exemplary approach, sensor 34 may output distance $\Delta$ to processor 40. In such an approach, processor 40 may calculate the amount of substance 30 based on distance $\Delta$. Accordingly, transmitter 36 may transmit the amount of substance 30 in container 16 rather than distance $\Delta$.

Transmitter 36 may transmit information about container 16 by interfacing with a receiver of a control unit 70, discussed below. Transmitter 36 may communicate wirelessly with receiver to transmit the information about container 16. The specific types of information that may be communicated will be addressed below. In one exemplary approach, the communication between transmitter and receiver is unidirectional with all transmissions originating from transmitter 36. However, other exemplary approaches may include a receiver with device 20 for implementing bi-directional communication. Transmitter 36 may include any of a number of transmitting technologies. Transmitter 36 may be a transceiver in that it may include a receiver to receive communications from other components, e.g., control unit 70. Communications received by the receiver may provide instructions to the processor 40, such as an instruction to activate the device 20 to determine the amount of the substance 30. Similarly, communications may include meta data 42 discussed below, for use by the device 20.

In one exemplary approach, transmitter 36 may be a radio frequency (RF) transmitter. RF transmitters emit signals in the radio frequency range of the electromagnetic spectrum. Within the domain of RF transmitters, any of a number of RF transmission standards may be employed by transmitter 36. The RF transmission standard generally defines the signal strength, frequency, data throughput, and communications protocol. Low power RF standards, such as Bluetooth®, Zigbee®, Wibree™, enOcean®, Zwave®, etc., are ideally suited for sensing and reporting device 20. In other exemplary approaches requiring greater data rates or transmission range, a radio frequency transmitter operating according to the wi-fi or wi-max transmission standards may be employed.

In yet another exemplary approach, transmitter 36 may be a radio frequency identification (RFID) circuit. In such an approach, an RFID circuit may act as both transmitter 36 and power source 38. The RFID circuit may include an antenna for transmitting RF signals. The antenna may also inductively generate electrical power when in the presence of an operating RFID reader.

In another exemplary approach, transmitter 36 may be an IR transmitter. The IR transmitter may include an IR diode that can produce an IR signal. The IR signal may then be received by a photoelectric receiver included with the receiver of the control unit 70. In another exemplary approach, transmitter 36 may produce a visible light signal. A visible light signal may produce a series of light pulses that may be received and interpreted by a receiver. Both an IR transmitter and a visible light transmitter typically rely on line of sight and therefore may be suited toward an implementation where line of sight communication is available or necessary.

In another exemplary approach, transmitter 36 may be an acoustic transmitter. For instance, transmitter 36 may be a speaker configured to audibly transmit the output of sensor 34. Transmitter 36 may announce the amount of substance 30 contained in container 16. Other acoustic transmitters may emit signals in an inaudible frequency for receipt and interpretation by an acoustic receiver.

While not depicted in the drawing figures, transmitter 36 may require an aperture in outer portion of lid 18. For instance, a non-metal aperture in a metal lid 18 may facilitate the transmission of radio frequency signals. Similarly, an IR transmitter may require a transparent or translucent aperture for the passage of the infrared signals and may further include a lens with the aperture. In another exemplary approach to reducing interference, not shown, transmitter 36 is provided on an outer surface of lid 18.

Power source 38 may provide electrical power to transmitter 35, sensor 34, and processor 40. The environment of kitchen 10 generally cannot accommodate a plurality of containers 16 wired to a power source. Accordingly, power source 38 may be an unwired power source allowing sensing and reporting device 20 to be self-contained and in some exemplary approaches, self-sufficient. Moreover, any of a number of unwired power sources may be employed as power source 38. Some examples of unwired power sources include a battery, a solar cell, an RFID circuit, as well as power sources that use at least one energy harvesting technique to derive power. Batteries, such as dry cell batteries, are well known for providing power to devices that cannot accommodate being wired to a power source. Dry cell batteries typically use a chemical reaction to provide power. As a result, batteries may become depleted over time. Accordingly a device with a battery power source may need to allow for replacement of the battery or may need to be disposable. A battery based power source may be implemented when the device 20 needs to be activated at arbitrary times as well as when the device 20 needs to be continuously activated. A battery may further act as a supplemental power source to other power sources discussed below. Solar cells, or photovoltaic cells, are known for implementing the photovoltaic effect to convert light energy into electrical energy. A cell disposed on an outer portion of the lid 18 could absorb light from the environment when removed from a containing unit 12. Solar and RFID based power sources are discussed in further detail below.

Energy harvesting techniques may include an inductive generator, a piezoelectric generator, a thermoelectric generator, a kinetic micro-generator, an electro-chemical generator and combinations thereof. Energy may be harvested, for example, from motion, forces, vibration, temperature gradients, ambient sources or a combination thereof.

An inductive generator may generate power from the movement of the lid. A source of magnetic flux may be associated with one of the lid and the jar and a flux responsive device may be associated with the other of the lid and the jar. The source of magnetic flux may be one or more permanent magnets attached to a surface of container 16, such as the rim of container 16. The flux responsive device may be a conductive coil extended along a circumferential surface of the lid, such as a lip portion of lid 18 that overlaps the rim of container 16. Spinning lid 18, which may be necessary to unscrew a screw-on lid, passes the coil through the magnetic fields provided by the magnets, which in turn induces a voltage between the ends of the coils.

A piezoelectric generator employs a material that demonstrates a piezoelectric effect. Applying a force or strain to the piezoelectric material may produce electrical energy that can be used by the elements of sensing and reporting device 20.

A thermoelectric generator may rely on a temperature gradient between two conducting materials to produce electrical energy.

Kinetic micro-generators may employ a moving element such as a pendulum, piston, flywheel, etc. to charge a capacitor which may in turn provide an electrical output. The moving element may cause an attached magnet to oscillate in the presence of a coil, which in turn charges the capacitor. The capacitor may then be discharged at the time the device 20 needs to be powered. A kinetic micro-generator may use piezoelectrics to harvest energy from ambient mechanical vibration.

A kinetic micro-generator may convert ambient vibration into electricity by placing magnets along a beam that is configured to vibrate in response to the ambient vibration. As the beam vibrates, the magnets move in response and move relative to a coil in proximity to the beam and the magnets. As the magnets move relative to the coil, electromagnetic induction causes current to flow in the coil. The current flow is the electric energy.

Solar cells and kinetic micro-generators are examples of power sources that derive their power from the natural ambient environment.

Power source 38 may provide power in response to accessing the substance of the container 16. Moreover, the time that container 16 is accessed is an ideal time to power sensing and reporting device 20 to determine the amount of substance 30 because container 16 is generally accessed for the purpose of removing a portion of substance 30. Therefore, sensing and reporting device 20 may be able to not only determine the amount of substance 30, but also may be able to calculate the portion of substance 30 removed with each access to container 16. However, if the activation of the device 20 is based on power generated from a movement there may be multiple sensor readings associated with an access of the container. Moving the container 16 may cause a reading while in transit. Removing the lid 18 may cause another reading, and affixing the lid may cause yet another reading. It may be desirable to take a reading both before and after an opening to determine the amount of the substance 30 removed or added. However, the difference between general movement, opening, and closing may need to be differentiated. Additionally, a delay in the activation of the device may allow for the substance 30 to settle prior to determining the amount. A capacitor may be included with power source 38 in order to store the electrical energy until it is needed. Processor 40 may cause the release of the electrical energy after the delay.

The choice of power source 38 may affect the specific time that sensing and reporting device 20 determines the amount of substance 30. For instance, a solar cell based power source may generate electrical power when container 16 is removed from an enclosed area such as refrigerator 12 or cabinetry 14 and exposed to a light source. A piezoelectric generator may generate electrical power as a result of the force or strain place on lid 18 during its removal. An RFID circuit may generate electrical power when exposed to an RFID reader. A thermoelectric generator may generate electrical power due to the temperature differential created when a container 16 is removed from refrigerator 12. While the power sources 38 just discussed may be able to automatically generate electrical power during the opening or closing of container 16, a battery based power source 38 may require the inclusion of an additional element in sensing and reporting device 20 such as a switch or an accelerometer in order to sense the opening or closing of container 16.

Processor 40 of sensing and reporting device 20 may be a general purpose microprocessor. Such a processor may provide a predefined instruction set that can be used to program device 20 with very flexible control software. However, in another exemplary approach, processor 40 may merely include circuitry to allow the level reading of sensor 34 to be transmitted by transmitter 36.

Processor 40 may include data 42, which may include at least one element of metadata. In one exemplary approach data 42 may be permanently embedded in processor 40. For instance data 42 may be a metadata element that provides an identifier. The identifier may identify the device 20, the container 16, the substance 30, or a class of the substance 30. Moreover, in an environment 10 including a plurality of containers 16, the identifier may uniquely identify a particular device 20. In another exemplary approach, data 42 may be dynamically modifiable. Processor 40 may include a memory storage device such as flash memory, an EEPROM, etc., which holds data 42. Sensing and reporting device 20 may additionally include a receiver to receive new data 42.

Data 42 is not limited to being only an identifier and may include many other possible items. Data 42 may include an indication of a prior amount of the substance 30. The prior amount compared to the current amount may allow for a determination of a portion of the substance 30 that has been removed. Data 42 may provide an indication of a chemical component of the substance 30. For instance, it may be desirable to know the chemical composition of the substance to make decisions regarding the environmental conditions of the substance 30, among other reasons.

Data 42 may include date and time values such as a date and time that the container 16 was first opened, a date and time that the container 16 was last opened, a date and time that the substance was processed or packaged at a processing facility. Data 42 may include manufacturing or processing information such as a name of the producer of the substance 30, a trade name of the substance 30, a generic name of the substance 30, an identifier of the processing facility that processed the substance 30, or a batch number of the substance 30. Data 42 may include nutritional and health information such as an indication of the nutritional attributes of the substance 30, an indication of the presence of allergens associated with the substance 30, and an indication of a dosage of the substance 30.

Data 42 may provide information for use in the determination of the amount of the substance 30 such as a lookup table mapping the output of the sensor 34 to the amount of the substance 30, or an indication of the physical dimensions of the container 16. Data 42 may be used to regulate and track usage of the substance 30 by providing a history of the amounts of the substance 30 as well as an indication of a permitted user of the substance 30. As will be discussed in more detail below, sensing and reporting device 20 may include additional sensors and accessory modules. Accordingly, data 42 may provide an indication of an ideal environmental condition of the substance 30, an output from an additional sensor, as well as a control parameter for an accessory module. Data 42 may further hold information from external sources such as sensors in the containing unit 12 or even information from other containers 16.

A control unit 70 may be provided in kitchen 10 for communicating with sensing devices 20. Control unit 70 may be integrated with an appliance as depicted, or may be a stand alone device. Similarly, control unit 70 may be provided as a peripheral of a PC or notebook computer. Control unit 70 may include a receiver and transmitter, not shown, for receiving communications from transmitter 36 of sensing and reporting device 20. The receiver of control unit 70 generally includes the same transmission technology as transmitter 36. However, if kitchen 10 includes sensing devices 20 with multiple transmission technologies, including any of those discussed above, control unit 70 may provide multiple receivers each configured to receive a respective type of transmission. In an approach using RFID circuits in sensing and reporting device 20, control unit 70 may provide an RFID reader for both activating and communicating with the RFID circuit.

Control unit 70 may provide a visual display 72 and a control interface 74 such as a key pad. In another exemplary embodiment, display 72 and control interface 74 may be integrated. Display 72 and control interface 74 cooperate to provide a user with facilities to control and interact with control unit 70 and sensing devices 20. In addition, control unit 70 with display 72 and control interface 74 may function as a user interface for refrigerator 12 or any other appliance like cooktops, ranges, dishwashers, washers, dryers, and the like, allowing the control unit 70 to send commands that effect the cycle of operation of the appliance. Interface 74 may display the amount of substance 30 in container 16 or cycle information about the cycle of operation of the appliance. Moreover, in a kitchen 10 with multiple containers 16, display 72 may show the amounts of substance 30 for each container. As discussed above, data 42 may include an identifier to assist the control unit 70 and the user in determining the amount of substance 30 associated with a particular container 16. Control unit 70 may allow a user to associate an identifier with a particular substance. For instance, if container 16 may be refilled with multiple different substances 30, control unit 70 may allow the user to associate a name or label with an identifier.

Figure 3:
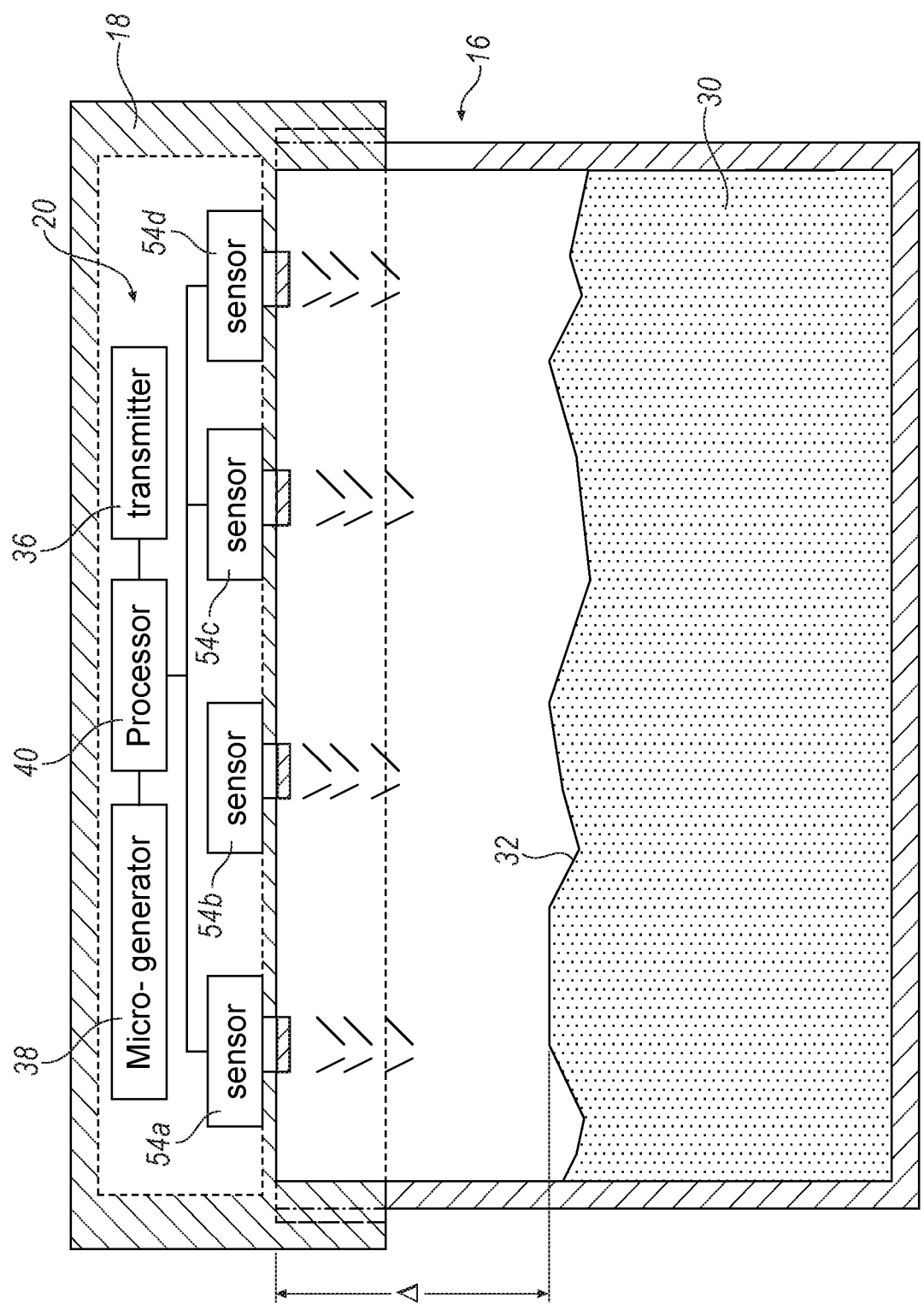
FIG. 3 is a partially schematic side, cut away, exploded view of a container including an alternate exemplary lid based device including multiple amount sensors.

FIG. 3 illustrates another exemplary container 16 having a sensing and reporting device 20 associated with the lid 18. As with the exemplary sensing devices discussed above, the device 20 of FIG. 3 includes a processor 40 and transmitter 36. The device 20 may be powered by a power source that may be a micro-generator 38, discussed below. Device 20 includes a plurality of amount sensors 54a-d. Each sensor 54a-d is distributed to different sections of the lid 18. Accordingly, each sensor 54a-d will read an indication of the amount of the substance 30 stored in the container at different points. Such an approach may be suited to determine the amount of substance 30 having an irregular surface level 32. The distance Δ between the surface level 32 and each sensor 54a-d may be different. A single distance Δ may be determined to a calculation, such as an average, of each reading of sensors 54a-d.

FIG. 4 illustrates another exemplary sensing and reporting device 20 having an additional sensor 56 and accessory modules such as an active device 58, a clock 62, and a user authorization module 64. As discussed above the additional sensor 56 may be a second sensor used to determine the amount of substance 30 in container 16. However, in another exemplary approach, the additional sensor 56 may be unrelated to the determination of the amount of substance 30. For instance, the additional sensor 56 may sense container attributes for determining the freshness or quality of substance 30. The active device 58 is one example of an accessory module that may be included with sensing and reporting device 20. Active device may operate to affect the substance. Active device may include a motor, an agitator, a fan, a dispenser, a dryer, a pump, a cooler, a heater, an ozone generator, etc. The active device may further affect the environment inside the container 16 above the surface level 32 of the substance 30. For instance, a pump may pressurize or depressurize the environment. A dryer may remove humidity from the environment. A fan or agitator may simply stir the air to create a circulation pattern. An ozone generator may produce ozone that can have preservative effects on certain kinds of substances 30, e.g., foodstuffs. A dispenser may emit substances necessary or useful to the substance 30, e.g., a preservative, etc.

Clock 62 may allow for the determination of the access times of container 16. The access times may be used to generate a usage history. Access times may also be used in cooperation with other date values such as the processing or production date of substance 30 in order to determine the freshness or quality of substance 30. Clock 62 may further allow the tracking of the amount of time that lid 18 is removed from container 16. Such information may further be useful in determining the freshness or quality of substance 30. User authorization module 64 may associate an individual to an access of container 16 and also to the removal of substance 30 from container 16. User authorization module 64 may provide an interface on an external surface of lid 18, e.g., a key pad, for accepting a user identification number. However, in another exemplary approach, sensing and reporting device 20 may further include a receiver, not shown, for bi-directional communication with control unit 70. A user may key in an identification number into the control interface 74 which would then be transmitted to sensing and reporting device 20.

FIG. 5 illustrates another exemplary sensing and reporting device 20. Some containers 16 may be manufactured without sensing and reporting device 20 integrated into lid 18. Moreover, a user may not want to have sensing and reporting device 20 in every container 16. Accordingly, common enclosure 50 may house the elements of sensing and reporting device 20 such as sensor 34, transmitter 36, power source 38, and processor 40. While common enclosure 50 could be fixedly attached to an inner surface 52 of lid 18, common enclosure 50 may allow sensing and reporting device 20 to be removably attached to inner surface 52. A removably attachable common enclosure 50 may allow sensing and reporting device 20 to be used in association with more than one container 16. Additionally, certain environments, e.g., a microwave, a dishwasher, may be harmful to the device. Accordingly, the common enclosure 50 may facilitate the removal of the device 20 at times when the container 16 will be subjected to harsh environments.

When transferring device 20 with common enclosure 50 to a different container 16, it may be desirable to associate data 42, such as an identifier, with the new container 16 or substance 30. Control unit 70 may control the association of identifiers to particular containers 16 or substances 30. For instance, control unit 70 may provide an interface in cooperation with display 72 and control interface 74 for identifying substance 30, container 16, etc., with data 42 when transferring sensing and reporting device 20 to a different container 16. Similarly, sensing devices 20 may be produced in bulk and packed as a dispensable roll of devices 20. Such an approach may be suited to a container 16 production or processing facility. At the time of dispensing, the metadata 42 may be set for the device 20.

Container based amount sensing devices 20, such as those described above, may be useful for various methods of inventory control. Exemplary inventory management systems are illustrated in FIGS. 6-10 described below.

Inventory control may implement inventory notifications in order to provide alerts related to the inventory. Notifications may be generated in response to triggering rules. The triggering rules may be based on the amount of substance 30 stored in a container 16 as well as other considerations. Other factors that may be included with triggering rules could include the time that a container is accessed, the amount of substance 30 that is added or removed, and the identity of the person that accessed the container 16. Inventory control methods include, among others, inventory monitoring, inventory usage restrictions, and inventory replenishment planning.

There are four primary variables that may be related to any access: the amount of substance 30 in the container 16, the type of substance 30, the access time and the identity of the individual accessing the container. These variables may be incorporated into notification triggering rules in order to provide access based notifications. An access of a container that includes a lid may be the opening or the closing of the lid. Other containers may be accessed through squeezing in order to dispense the substance 30. Similarly, a container may include a regulator, such as a spigot for dispensing the substance 30. Accordingly, an additional variable may be the type of access event, e.g. opening, closing, substance removal, substance addition, dispensing, filling, removing the container 16 from a storage unit, etc.

It should be apparent that all possible variables have not been enumerated and that one skilled in the art will recognize other variables that may be included with notification triggering rules. Notifications that are provided at the time of opening may be considered opening or pre-access notifications while notifications that are provided at the time of closing may be considered closing or post-access notifications. The sensing and reporting device 20 may be configured to provide an indication of the amount of the substance 30 at the time of opening, closing, or both, as well as at other times.

Figure 6:
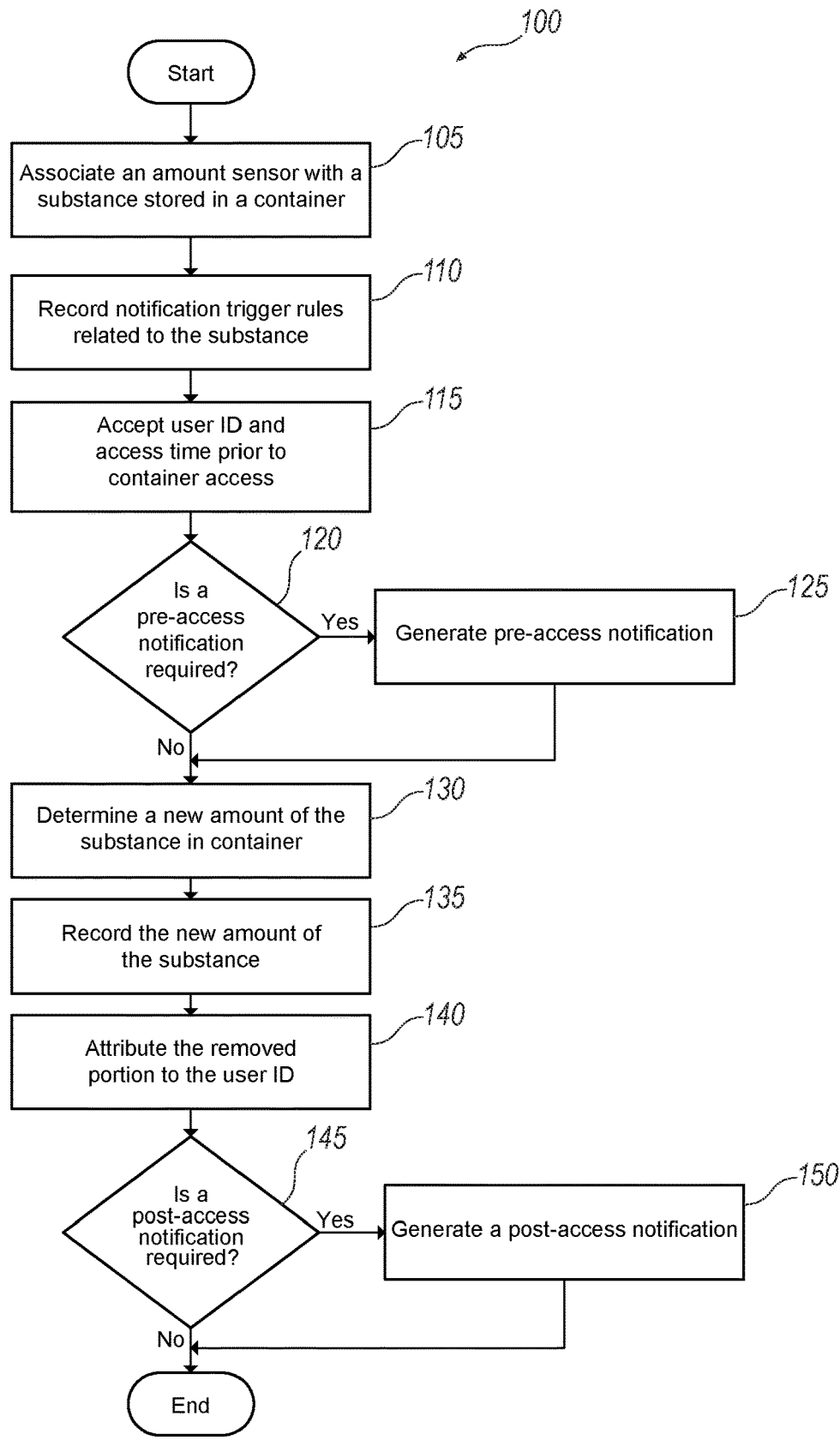
FIG. 6 is a flowchart depicting exemplary steps and procedures related to an inventory management system that provides notifications based on the user ID and the amount of substance stored in a container.

FIG. 6 illustrates a flowchart depicting exemplary steps and decisions related to activating a container and generating access based notifications. Process 100 presents a generic representation of an access based notification method for inventory control. Processes 200 and 300, discussed below, present implementations of process 100 as applied respectively to the storage of medications and foodstuffs. Process 100 describes notifications as either pre-access or post-access notifications. It will be recognized that other exemplary processes may omit either the pre-access or post-access notifications. For instance, an exemplary process may only provide notifications subsequent to the accesses and removal of a portion of the substance 30.

Process 100 begins in step 105 where a sensing and reporting device 20 may be activated by being associated with a substance 30 stored in a container 16. Additionally, the association may be recorded or stored by control unit 70. In one exemplary approach, containers 16 with sensing and reporting device 20 may provide a generic and reusable storage medium. An operator may fill the container 16 with any type of substance 30. Moreover, once empty, the container 16 may be refilled with a different type of substance 30. Accordingly, the association allows the control unit 70 to track which of potentially many substances is currently being stored in container 16.

An environment 10 may include multiple containers 16, each storing a substance 30. The substance stored in a container 16 may be the same or different from a substance 30 stored in a different container 16. In another exemplary approach, the sensing and reporting device 20 may be removable from the container 16. Accordingly, the association may be both a physical association of the device 20 to a container 16 as well as a data association of the device 20 and the substance 30. In another exemplary approach, a producer or processor of the substance 30 may prepackage the substance in a container 16 that includes an amount sensor 20. In such an approach, the identifier of the sensing and reporting device 20 would be unknown in the environment 10. Accordingly, the identifier and the association to the substance would both need to be entered into the control unit 70.

An initial amount of the substance may be determined and stored at the time that the association is entered at the control unit 70. The initial amount may facilitate the determination of an amount added or removed at the time a container 16 is accessed. The control unit 70 may store a brand name of substance 30, a generic name of substance 30, a name of a class of substance 30, etc. in association with the identifier.

Next, in step 110, notification trigger rules related to substance 30 may be stored in the data store. In an alternative approach, triggering rules may be associated with a container 16. Associating a triggering rule with a substance 30 may facilitate the generation of notifications across a plurality of containers 16 containing the same type of substance 30. The control unit 70 may provide a user interface for entering one or more triggering rules.

The trigger rules may include any type of information related to the substance 30 that will be used to trigger an access notification. The trigger rules may be correlated to a user ID of a particular operator. The user ID may be any type of information or data that identifies a user, e.g., a name, or an ID number. The trigger rules may further be related to at least one amount of the substance such that a triggering event may be based on the combination of the user ID, the substance 30, and the current amount of the substance 30. Triggering rules may further depend on time values such that a notification is only triggered at certain times. Triggering rules may depend on the type of access, e.g., opening, closing, substance 30 addition, substance 30 removal, etc. Combinations of any of the user ID, amount, and date/time may be provided to create complex triggering rules. For instance, a triggering rule may be based on a user ID, a date, and an amount. Triggering rules may be also dependent on other environmental factors, such as seasonal changes, anticipated changes, and consuming pattern changes including but not limited to the change of the number of consumers. Additionally, the amount and date may be associated with comparison technique such that triggering rules can specify that an amount or date should, for example, be less than a certain value. Each container may have a plurality of triggering rules associated therewith. Triggering rules generally may be evaluated to a Boolean true or false result.

Next, in step 115, a user ID and access time may be recorded prior to, or contemporaneously with, accessing container 16. Providing a user ID contemporaneously with an access of the container 16 may allow for pre-access notifications generated by triggering rules based on the user ID. However, in an alternative approach that does not need user-specific pre-access notifications the step of collecting of the user ID prior to access may be omitted. Control unit 70 may maintain a log in a data store of all notifications. The log may include a sequence of date ordered entries or line items. The log may be implemented in a database with each entry being a database record or row. In one exemplary approach, an operator uses control interface 72 of control unit 70 to provide a user ID. Control unit 70 may include an internal clock to record the access time. The user ID and access time may be stored to a data store as an entry in an access log. Additionally, the entry may indicate that the operator intends to access at least one container 16. Once a particular container 16 is accessed, the access log may be updated with an additional entry identifying the container 16 that was accessed. If the operator accesses more than one container 16, an access log entry may be stored for each container 16.

Next, in step 120, it may be determined whether a pre-access notification is required for the container 16 that has been accessed by the operator. The triggering rules stored in data store may be queried based on the identifier of the container 16. Any resulting triggering rules may be evaluated with applicable date, amount, and user ID values. Any rule that evaluates to a Boolean true result may cause a notification to be generated. If all triggering rules for the substance 30 result in a false result, the process may skip to step 130.

Next, in step 125, a pre-access notification may be generated. The pre-access notification may be related to the triggering rule that evaluated to a true result. If more than one triggering rule evaluated to a true result, then a pre-access notification may be generated for each rule. The notification may include the values of the triggering rule in order to provide an explanation for the notification. For instance, if the triggering rule is based on an amount level, the notification may indicate that the amount of substance 30 has been depleted to the specified triggering level. The notification may be provided to the operator via the display 72 of control unit 70, audibly, through an entry in the log stored in the data store, etc. Additionally, the notification may be distributed to remote recipients, e.g., via an email message, or the like.

Next, in step 130, a new amount of substance 30 may be determined. It is to be understood that the operator may have removed some of the substance, added additional substance, or neither added nor removed any of the substance. As discussed above, sensing and reporting device 20 may be configured to activate at the time of closing the lid 18. Affixing lid 18 to container 16 may activate sensing and reporting device 20 to determine the amount of substance 30 currently contained in container 16. The new amount may then be transmitted to control unit 70 as discussed above.

Next, in step 135, the new amount may be stored to a data store. Accordingly, the new amount will be available for use in step 120 in a future access of container 16. The new amount may be established as the current amount. The previous current amount, which may have been the initial amount, may be stored as a historical amount. Accordingly, the data store of control unit 70 may track the usage of substance 30 by recording the amount each time the lid 18 is closed or affixed to container 16.

Next, in step 140, the removed portion may be attributed to the user ID. The previous amount and the current amount may be used to calculate a portion that is the difference between the two amounts. The portion may represent added or removed substance 30. The portion, user ID, and date and time may be stored to the data store and associated with the substance 30. Accordingly, the data store may keep a running log of not only the historical amounts of the substance 30, but also a historical log of the usage of the substance 30 that may be attributed to the operator. In an alternative approach that does not store historical amounts, a reading of the amount may be obtained from the sensing and reporting device 20 prior and subsequent to an access. Accordingly, the portion may be the difference between the prior and subsequent amounts.

Next, in step 145, it may be determined whether a post-access notification is required. As discussed above with respect to step 120, the notification trigger rules associated with sensing and reporting device 20 may be evaluated. The rules may be re-evaluated even if the current amount is the same as the previous amount given that a trigger rule may be based on other factors such as the time. A triggering rule may trigger a post-access notification based on a new amount of the substance 30. Other exemplary triggering rules may trigger notifications based on timing such as the time of the evaluation, the length of time between the pre-access and post-access evaluation, etc. The length of time between the pre-access and post-access evaluations may be indicative of the length of time that a container 16 is open, or the length of time container 16 is outside of storage.

Next, in step 150, a post-access notification may be generated. As in step 125 above, the notification may be provided to the operator via the display 72 of control unit 70, audibly, through an entry in the log stored in the data store, etc. Additionally, the notification may be distributed to remote recipients, e.g. via an email message, or the like.

Following step 150, process 100 ends. Accordingly, process 100 may allow for access based notifications that are triggered according to information about the substance 30 in correlation to the time of access, a user ID, the amount of substance 30 added or removed from the container 16, etc.

Figure 7A:
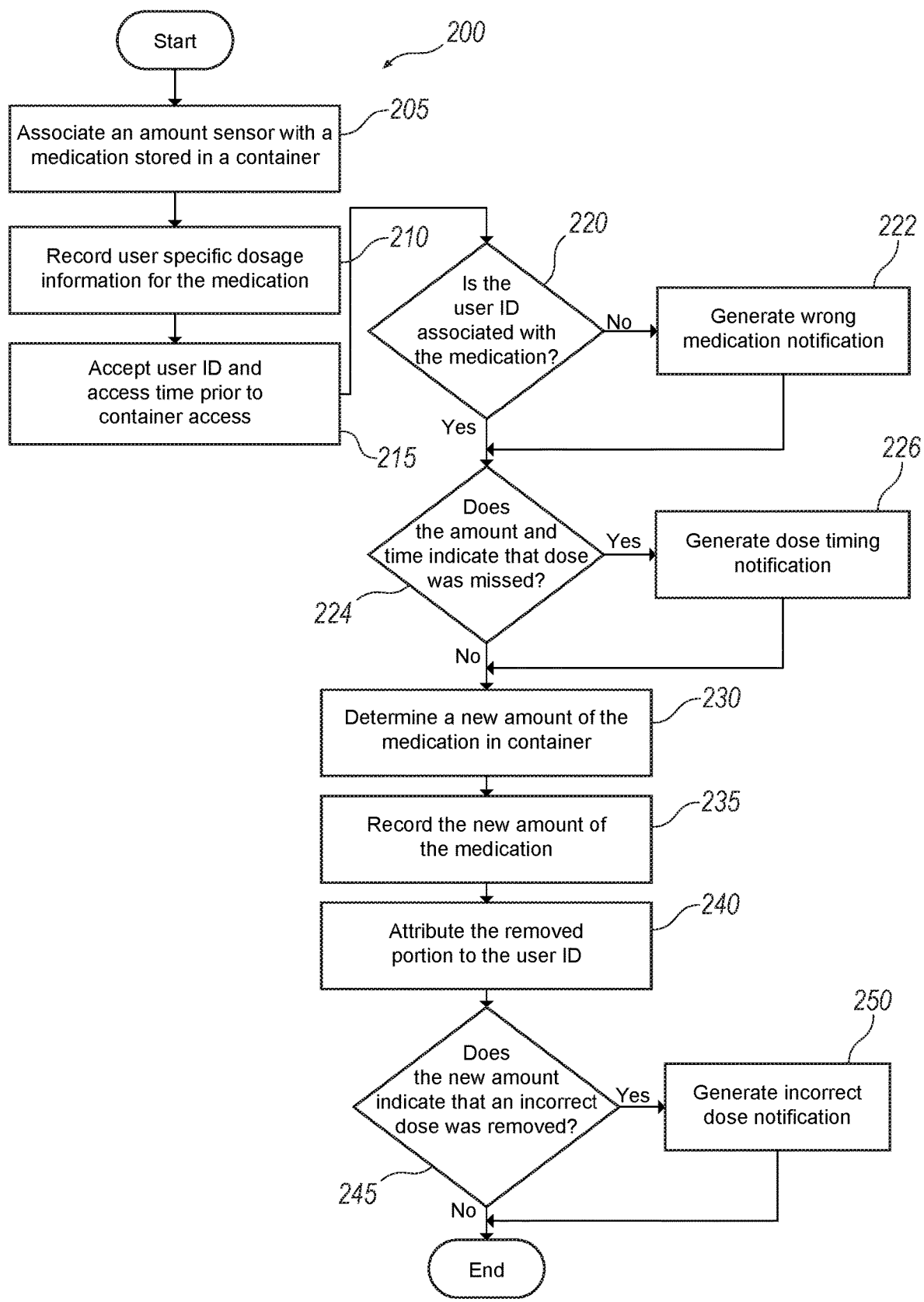
FIG. 7A is a flowchart depicting exemplary steps and procedures related to a medication management system that provides notifications based on the user ID and the amount of medication stored in a container.

FIG. 7A illustrates a flowchart depicting exemplary steps and decisions related to a process 200 for regulating and monitoring the access of a medication substance 30 contained in a container 16 having a sensing and reporting device 20.

Process 200 begins in step 205 where a sensing and reporting device 20 may be associated with a medication substance 30. The sensing and reporting device 20 of container may include an identifier as an element of data 42. The identifier may be correlated to the medication stored in container 16.

Next, in step 210, dosage information related to a particular operator and medication may be stored in a data store. The dosage information may include scheduling or timing of doses as well as dose amounts. The dosage information may be extrapolated to determine a set of expected amounts at specific times. For instance, at each scheduled dose time, the amount may be reduced by the dose amount. Accordingly, this chart/table of amounts and times may be used in the determination of whether a dose was missed. In an alternative approach, the timing and amount of the next dose may be based on the most recent dose rather than a predetermined dose schedule. For instance, if a dose is taken at a time that does not correspond to a time on the dose schedule, the schedule may have to be updated so that a dose time notification is not perpetually generated. Determining dose time based on the previous access time may eliminate the need to calculate and recalculate a complete dose schedule. The dose timing may be stored as one or more notification trigger rules.

Next, in step 215, access data such as the user ID of the accessor or user as well as an access time may be recorded. Step 115 above provides additional details related to the collection and processing of access data.

Next, in step 220, it may be determined whether the operator is associated with the medication. A triggering rule may provide a correlation between the user ID and the medication. However, in another exemplary approach, a dedicated set of records that are not notification trigger rules may provide a correlation between the user ID and the medication. The data store may be queried based on the user ID and the identifier to determine if there is a correlation. If no correlation exists between the user ID and the medication, then it may be determined that the medication should not be removed by the operator.

Next, in step 222, a wrong medication notification may be generated. Step 115 above describes various ways of providing the notification. It is to be understood that the operator may remove a portion of the medication despite receiving a wrong medication notification. Accordingly, the process continues.

Next, in step 224, it may be determined whether the current amount of medication in the container 16 as well as the time of access indicates that a dose was missed. For instance, if the current amount exceeds an expected amount for the given time of access, it may be concluded that a dose was missed. In an alternative approach, the determination of whether a dose was missed may be based only on the access time and not on the amount of medication in the container. The access time may be compared to a predetermined schedule of dose times or may be based on the previous access time and the standard dose period.

Next, in step 226, a dose timing notification may be generated. The dose time notification may include instructions on the amount of medication that should be removed. The amount that should be removed may be the standard dose amount or may be some amount less than the standard dose amount. For instance, if the prior dose was an under dose, an amount corresponding to the difference between the standard dose and the under dose may be an acceptable amount. Step 115 above discusses ways of providing the notification. Additionally, the notification may be distributed to health care providers and the like.

Next, in step 230, a new amount of the medication may be determined. For instance, sensing and reporting device 20 may be activated in response to affixing the lid 18 to container 16. Determining the amount at the time of container closing allows for a determination of whether any medication was removed or added.

Next, in step 235, the new amount of the medication 30 stored in the container 16 may be recorded. Recording the amount removes the need to determine the current amount when opening the container 16. However, in another exemplary approach, the new amount of medication 30 does not necessarily need to be stored if the amount can be determined at the time of accessing the container 16.

Next, in step 240, the portion of medication removed from the container 16 may be attributed to the operator. The portion may be determined based on the difference between the current amount and the most recent previous amount. As discussed above, the attribution may be stored to a log file. The log may be included with a medical history of the operator.

Next, in step 245, it may be determined whether the new amount indicates that an incorrect dose was removed. The portion may be compared to the standard dose. A portion exceeding the standard dose may indicate an over dose and a portion less than the standard dose may represent an under dose. In another exemplary approach, the portion may be summed with a prior portion if the prior portion represented an under dose and the current portion was removed during the same dose period as the prior portion. As discussed above, the dose schedule may need to be updated with a new set of expected amounts using the current amount as a base value that is offset by the standard dose amount. In another exemplary approach, a notification trigger rule may be created for the next access based on the current amount as well as on the current time. In such an approach, each notification trigger rule would be based off the most recent access rather than by a predetermined schedule.

Following step 245, process 200 ends. Accordingly, process 200 provides exemplary steps and decisions related to providing access based notifications for a medication stored in a container 16 with a device 20 configured to determine an indication of the amount of medication contained therein.

Figure 7B:
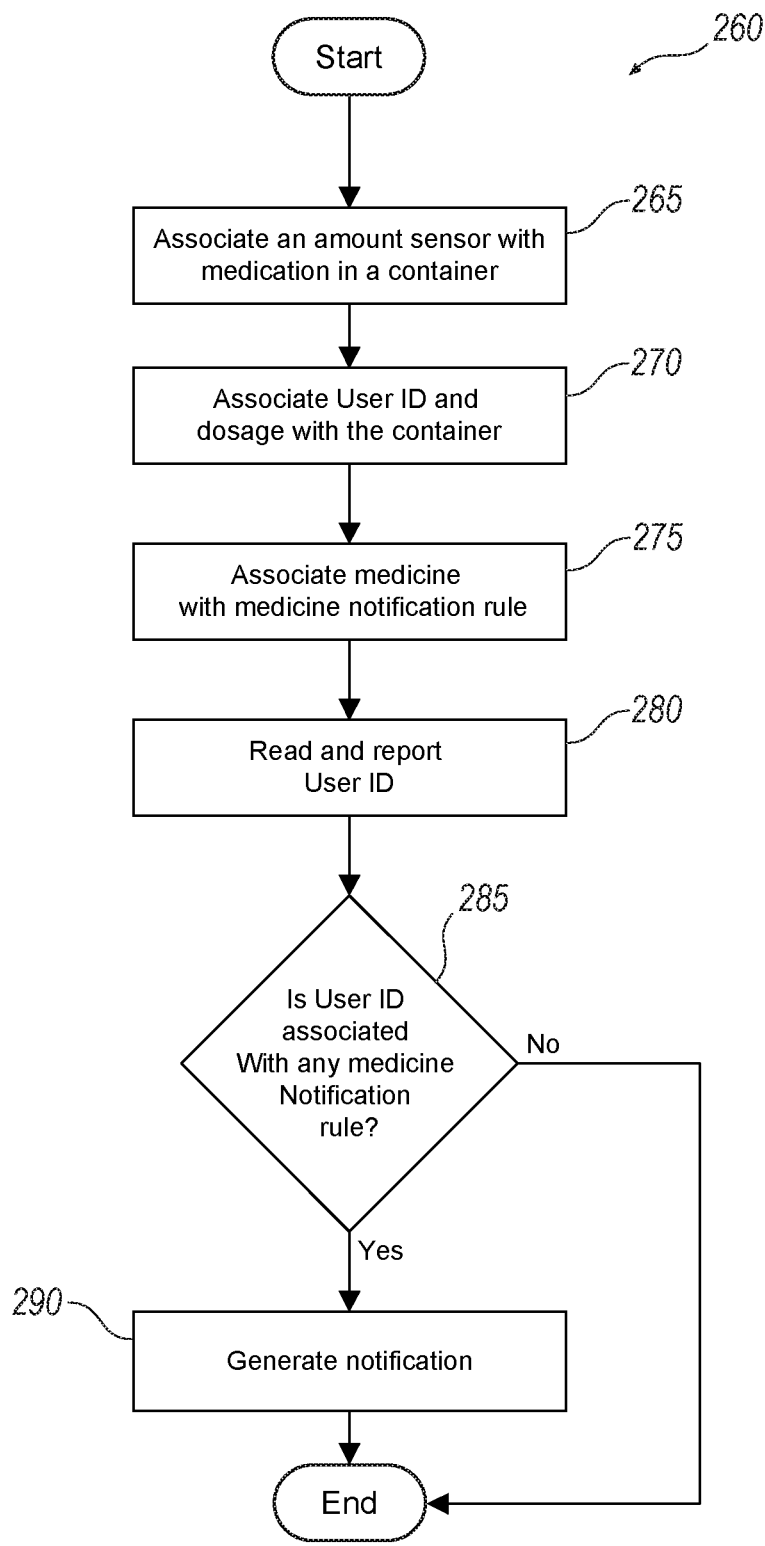
FIG. 7B is a flowchart similar to FIG. 7A but depicting exemplary steps and procedures related to a medication management system that provides notifications based on user identification, dosage information and reminders to take medicine.

FIG. 7B illustrates a flowchart depicting alternative exemplary steps and decisions in a process 260 similar to process 200 described above. Some or all of the steps of process 260 may be substituted for steps of process 200 or may be added to process 200.

Process 260 begins in step 265 where a sensing and reporting device 20 may be associated with a medication substance 30.

Next, in step 270, dosage information and user ID information is associated with medication substance 30. The user ID information may itself be associated with a patient or with a caregiver or both. Step 270 may occur at the pharmacy at the time of filling the prescription by adding the information to data storage incorporated into the container or lid or by providing it on the container in a machine readable fashion. The information may be subsequently communicated to a central data system in the use environment, such as smart refrigerator or smart medicine cabinet, or may be inputted by the patient or caregiver at the time the medication substance 30 is introduced into the use environment.

Next, in step 275, a medicine notification rule may be associated with the user ID. The rule may be a standard notification rule derived from the dosing schedule or may be a medicine specific rule provided by the physician, the dispensing pharmacy or the user. Alternatively, it may be retrieved from a database of rules associated with various medicines by their manufacturers. It may also include as inputs information about the patient, such as age and medical condition.

Next, in step 280, an event including a user ID may be reported. The event may be an access event such as opening a container or dispensing medicine. Alternatively, the event may be a user entering the use environment or opening a storage compartment holding the medication substance 30, such as a smart refrigerator or smart medicine cabinet. The notification rule may be different for a user ID for a patient than for a user ID for a care giver.

Next, in step 285, it may be determined whether the user ID reported is associated with a medicine notification rule. If a notification rule exists, then the notification rule is consulted to determine what type of notification should be provided.

Next, in step 290, a notification may be generated if appropriate according to the notification rule. The notification may be, for example, a reminder that medicine is due at some time in the future, a reminder that medicine is now due, a reminder that medicine is over due or a reminder that medicine needs to be ordered. The reminder may include dosage or other dispensing information, such as a reminder to eat or not eat with the medication, or a warning about drug or food interactions. The notification may combine information about multiple medicines associated with a patient and may report historical medicine consumption information relating to the patient, including information about prior adverse reactions.

Following step 290, process 250 ends.

Accordingly, process 250 provides exemplary steps and decisions related to providing access based notifications for a medication stored in a container 16 with a device 20 configured to assist a patient or care provider in the management of medicine consumption.

Figure 8:
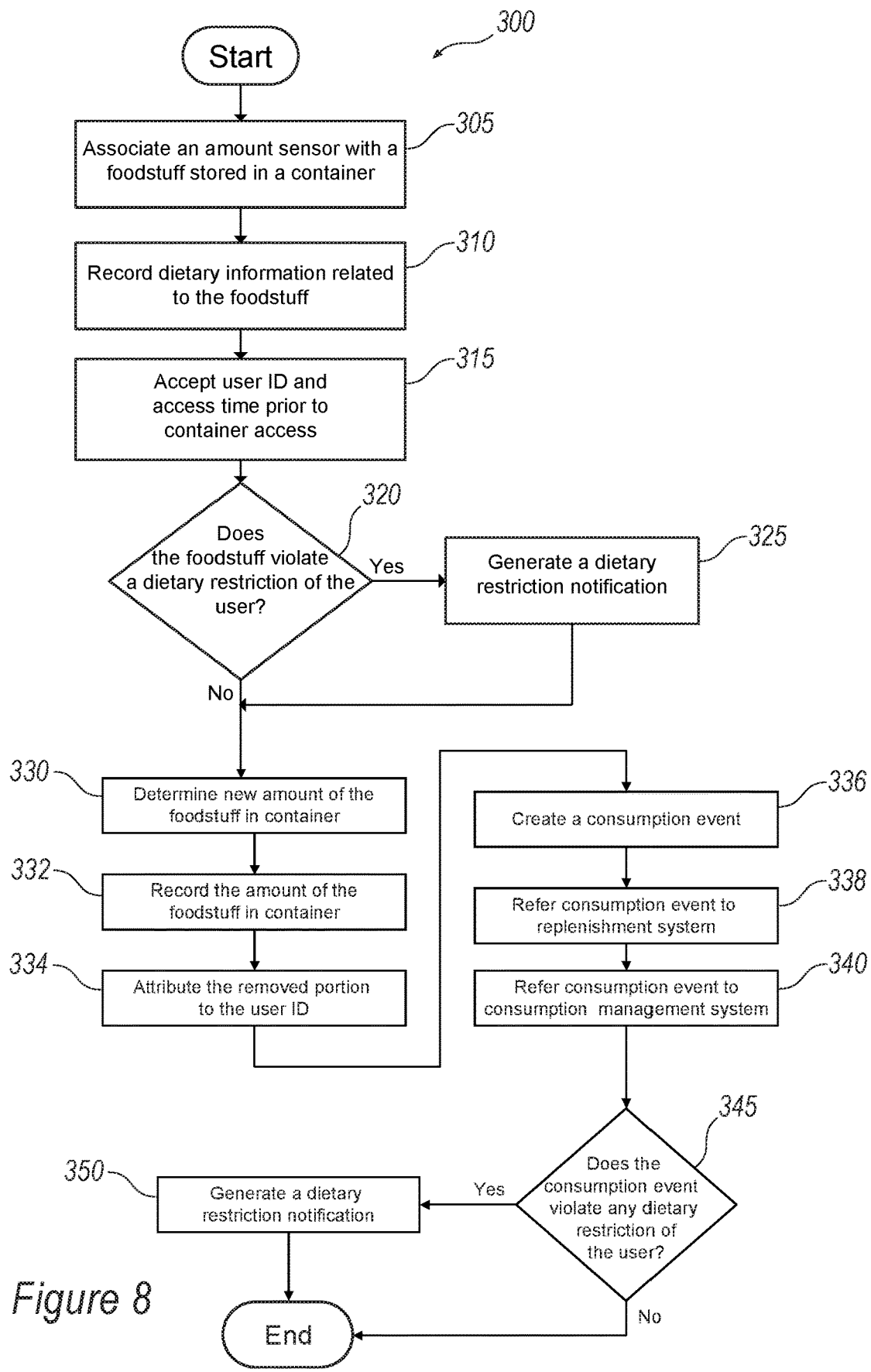
FIG. 8 is a flowchart depicting exemplary steps and procedures related to a dietary management system that provides notifications based on the user ID and the amount of a foodstuff stored in a container.

FIG. 8 illustrates a flowchart with exemplary steps and decisions related to a process 300 of managing an inventory of a foodstuff with respect to dietary restrictions.

Process 300 begins in step 305 where a sensing and reporting device 20 may be associated with a foodstuff. As discussed above, associating the sensing and reporting device 20 with the contents may facilitate the creation of trigger rules based on the substance 30. Accordingly, the foodstuff may be identified by type or brand name and associated with the sensing and reporting device 20.

Next, in step 310, dietary restrictions related to the foodstuff may be recorded. Dietary restrictions may include foodstuffs that should not be consumed by an individual for health or allergy reasons. Additionally, dietary restrictions may be related to a quantity of the foodstuff that may be consumed by an individual. Dietary restrictions may set out certain combinations of foodstuffs that should be avoided. The dietary restrictions may be stored as one or more notification trigger rules.

Next, in step 315, the user ID may be accepted from the individual accessing the container 16. Accepting the user ID may allow for the retrieval and evaluation of notification trigger rules based on the user ID.

Next, in step 320, it may be determined whether a dietary restriction notification should be generated. Using the provided user ID, the notification trigger rules may be queried. Any notification trigger rules related to the user ID may then be evaluated.

Next, in step 325, a dietary restriction notification may be generated. An evaluated notification trigger rule may indicate that the user associated with the user ID should avoid consumption of the foodstuff contained in the container 16. In another approach, the notification may provide the individual guidance with respect to an amount that may be consumed, taking into account food interactions, specific or general daily nutritional requirements, specific or general daily consumption limits, kosher or other dietary laws, reservations of food or nutritional categories for later consumption, elevated market price for replenishment, or other criteria. In still another approach, in which multiple containers 16 are accessed, the notification may be based on the combination of the foodstuffs.

Next, in step 330, an amount of the foodstuff may be determined. The sensing and reporting device 20 may be activated in order to produce an indication of the amount of the foodstuff. This indication of the amount may reflect a different amount than the prior amount if the amount was altered by the accessing individual.

Next, in step 332, the latest amount may be recorded. Recording the amount may facilitate the determination of portions that have been removed or added. Similarly, recording the amount may provide a historical record of the amount of the foodstuff.

Next, in step 334, the removed portion, if any, may be attributed to the user ID. Attributing the removed portion may facilitate the planning and tracking of a nutritional plan or may be used to allocate the cost of replenishment. The removed portion, combined with other portions including portions of other foodstuffs, may indicate whether the individual is consuming a desired degree of nutrition. For instance, the nutritional plan may be a weight loss diet and the portions may indicate whether the diet is being followed.

Next, in step 336, a consumption event may be created for use by an inventory management system. The consumption event may include the type of foodstuff, the user to which it is attributed, the time and date of consumption, and the quantity consumed. For example, in step 338, the consumption event may be referred to a replenishment system for tracking the use and consumption of foodstuff and managing the replacement of foodstuff. In step 340, the consumption event may be referred to a user consumption management system for tracking the consumption habits of a user and generating dietary recommendations or notifications. Similarly, the consumption event could be referred to an inventory system for managing the level and use of inventory for budgetary purposes. Alternatively, the consumption event could be referred to a recipe management system for generating proposed recipes for the foodstuff in inventory.

Next, in step 345, it may be determined whether a dietary restriction has been violated and dietary restriction notification should be generated. A notification trigger rule may indicate a maximum, minimum or recommended portion size that should be consumed. Similarly, the rule may indicate a time that the portion should be consumed. A notification may be generated if, for instance, the portion does not correspond to a portion established in a notification trigger rule. A notification may propose an alternative foodstuff or activity.

Next, in step 350, a dietary violation notification may be generated. The violation notification may indicate that a foodstuff that should not have been consumed was consumed, that an improper portion was consumed, that a portion was consumed at an improper time, etc. In addition to the ways of providing the notification discussed above in step 125, the notification may be provided to an external source such as a nutritional planning or dietician system. It should be noted that notification can occur after an access event but before removal or dispensing of foodstuff from the container, after removal or dispensing of foodstuff, or both.

Following, step 350, the process 300 ends. Accordingly, process 300 provides exemplary steps and decisions related to providing access based notifications for a foodstuff stored in a container 16 with a device 20 configured to assist the user in complying with dietary restrictions.

Figure 9:
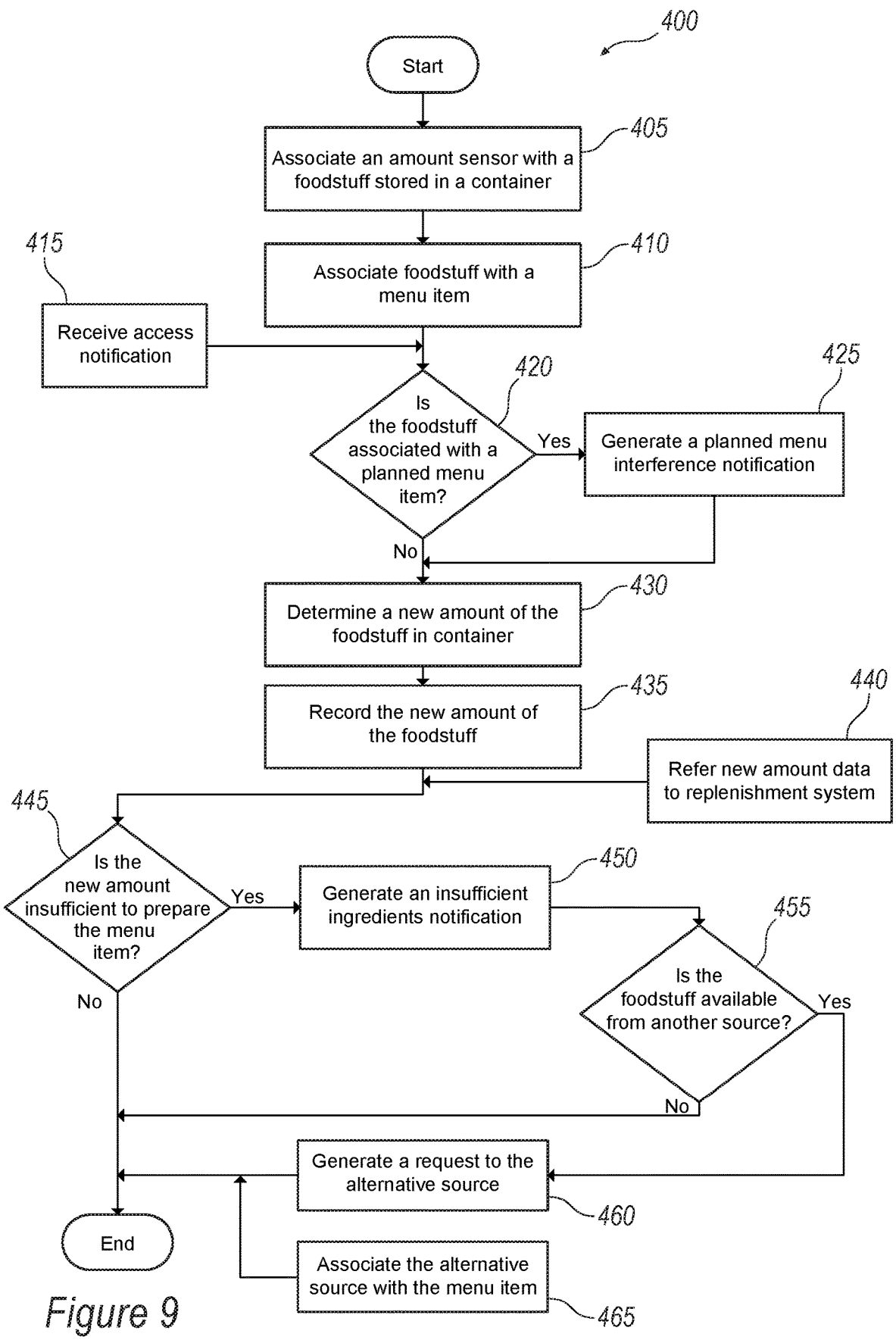
FIG. 9 is a flowchart depicting exemplary steps and procedures related to an inventory management system that provides notifications based amounts of the substance that are reserved for a future use.

FIG. 9 illustrates a flowchart with exemplary steps and decisions related to a process 400 of managing an inventory of foodstuffs with respect to planned menu items. Process 400 includes pre-access and post-access notifications. However, unlike processes 100, 200, and 300 user identification may not be required in process 400. User identification could be added if, for instance, multiple food preparers need to track which food preparer is utilizing a foodstuff. Such identification may be desirable in an environment where food preparers are individually responsible for the foodstuffs, e.g., roommates that purchase their own food.

Process 400 provides a specific example to a more general concept of resource planning. For instance, the substance 30 in the container 16 is not required to be a foodstuff and the planned menu item is not required to be a prepared meal. The planned menu item could be generalized as any use of the substance 30 that is planned for the future. A portion of the substance 30 may be reserved for the planned use in the future.

Process 400 begins in step 405 where a foodstuff may be associated with a sensing and reporting device 20. Steps 105 and 305 above discuss such an association.

Next, in step 410, at least one planned menu item may be recorded to a data store and the foodstuff on the menu item is associated with the menu item. The planned menu item may be stored as one or more notification trigger rules which relate to the foodstuff. The trigger rule may indicate a minimum amount of the foodstuff that is reserved for the planned use in the menu item. The planned menu item trigger rule may further include a time of the future use as well as any known replenishment dates.

Next, in step 415, an access notification is received indicating that container 16 has been accessed.

Next, in step 420, it may be determined whether an accessed container 16 stores a foodstuff that is associated with a planned menu item. The sensing and reporting device 20 may be activated to provide an indication of the amount. The amount and the substance identifier may be used to retrieve any associated notification trigger rules. The trigger rules may be evaluated to determine if the foodstuff will be used with a planned menu item and may further be evaluated to determine if there is currently a sufficient amount of the foodstuff for the planned menu item.

Next, in step 425, a planned menu interference notification may be generated. The notification may simply indicate that the foodstuff will be used in a planned menu item. Additionally, the notification may provide an indication of the amount that should be reserved for the future use. For instance, the notification may instruct the accessing individual to leave at least a certain amount for the planned menu item. Similarly, the notification may provide the accessing individual with the maximum amount that may be removed without disrupting the planned menu item.

Next, in step 430, a new amount of the foodstuff may be determined from the sensing and reporting device 20. The current amount may differ from a previous amount if the accessing individual added or removed any of the foodstuff.

Next, in step 435, the new amount of the foodstuff may be stored. Storing the new amount may facilitate the determination of the amount removed or added by the accessing individual. In another exemplary approach, the user ID of the accessing individual may be provided in order to associate the portion removed with the user ID.

Next, in step 440, the new amount may be referred to a replenishment management system, for example, for dynamically responding to the access event by determining if replenishment action is required for the foodstuff being accessed.

Next, in step 445, it may be determined whether the new amount is insufficient for preparing the planned menu item. The notification trigger rule may be evaluated again in light of the new amount. If the new amount exceeds the minimum reserved amount specified in the notification trigger rule then the new amount may be considered sufficient. If the new amount is sufficient, then process 400 may end.

Next, in step 450, an insufficient ingredients notification may be generated. The notification may simply indicate that the planned menu item cannot be produced. In another exemplary approach, the notification could add the foodstuff to a shopping or replenishment list. Similarly, the notification could be sent to an automated replenishment system. The notification may indicate the amount that is needed in order to produce the planned menu item.

Next, in step 455, it may be determined whether the foodstuff is available from another source. An alternative source could be a nearby location, e.g., a neighbor. The inventory system may be linked via a network to communicate with other inventory systems. Accordingly, the linked or associated inventory systems may be queried to determine if there is a sufficient amount of the foodstuff that could be used for the planned menu item without interfering with a planned menu item at the associated inventory system. In another exemplary approach, the alternative source may be from one or more substitute ingredients. For instance, some foodstuffs may have equivalents or substitutes that may be used in place of the insufficient ingredient. A table of substitutes may be maintained and queried to determine a suitable substitute. The amount of the substitute may then be determined to see if it could be used to produce the planned menu item. If there are no alternative sources of the foodstuff, process 400 may end. However, in an alternative approach, rather than ending the process may scale down the planned menu item to accommodate the amount of the foodstuff that is available. For instance, if only half of the necessary foodstuff is available, all other required ingredients may be scaled down by half in order to make a half portion of the planned menu item. In another approach, rather than scaling down the planned menu item, the system may use the knowledge of the amounts of each substance being tracked to suggest alternative menu items that may be produced with the available ingredients.

Next, in step 460, a request for the ingredient may be generated and sent to the alternative source. As discussed above, the request for the ingredient may also be provided to a replenishment system or may be added to a replenishment list.

Next, in step 465, the alternative source is associated with the menu item to reserve a portion of the alternative source for later use.

Following step 465, the process may end. Accordingly, the inventory system may be used to reserve an amount of a substance for a future planned use. As the specific example provided above detailed, foodstuff ingredients may be reserved for future planned menu items. Substitutes and alternative sources of the reserved amount may be sought for any insufficient amounts.

Figure 10:
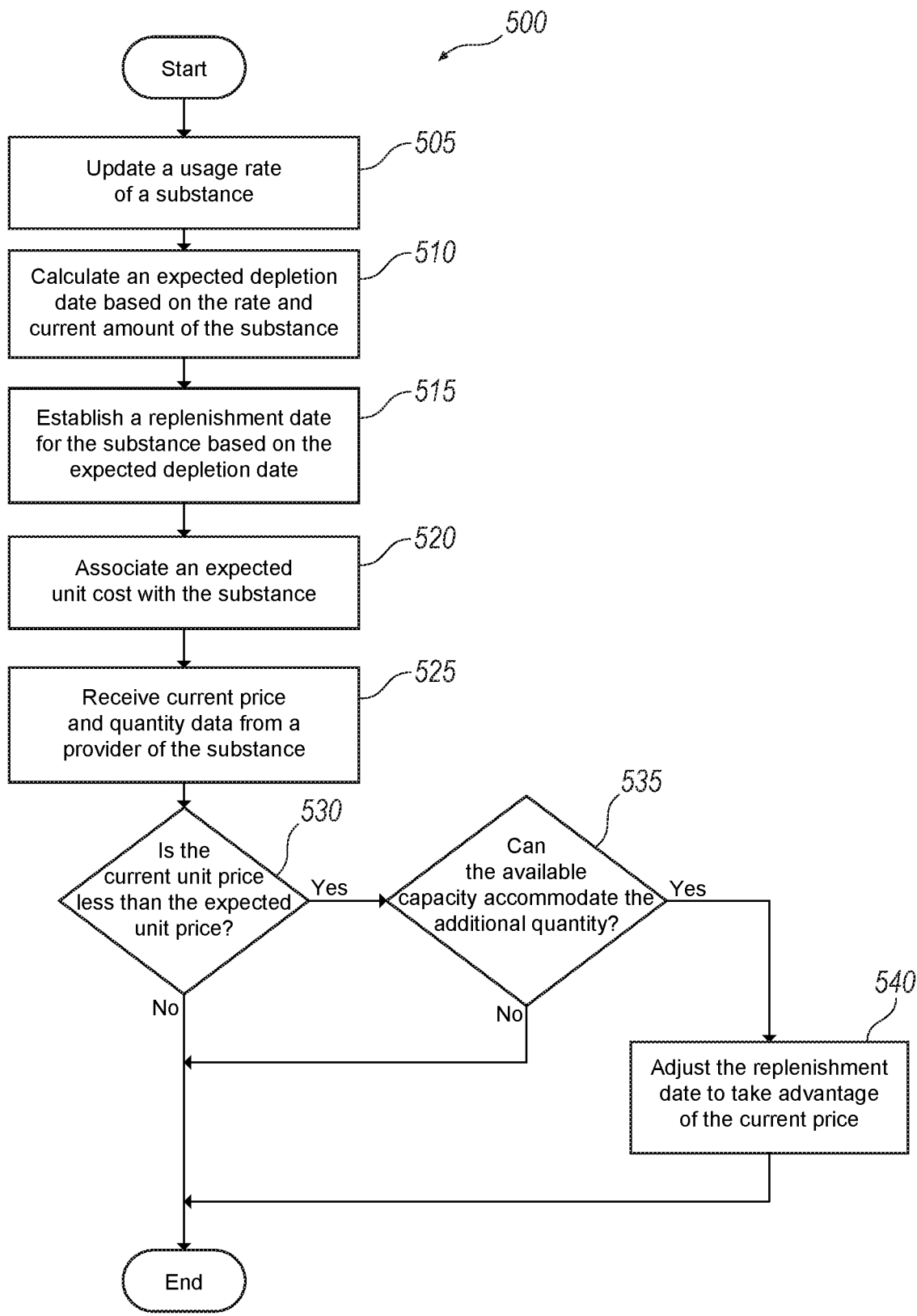
FIG. 10 is a flowchart depicting exemplary steps and procedures related to an inventory management system that calculates usage rates and replenishment dates.

FIG. 10 illustrates a flowchart with exemplary steps and decisions related to a process 500 for calculating and updating replenishment dates of substances 30. Substances 30 may need to be replenished as they are used or consumed. Determining the replenishment date may be based on only the current amount as indicated by the sensing and reporting device 20 or may be based on historical usage patterns. Tracking the amount of the substance 30 over time may provide an indication of the historical usage pattern or rate.

Process 500 begins in step 505 where a usage rate of a substance may be updated. It is to be understood that process 500 is a continuous process, so an existing usage rate may already exist. However, at the initialization of the process, a default usage rate might be provided. In another exemplary approach, there may be an initialization period in which usage is tracked in order to provide an initial usage rate. The usage rate may be updated by taking a reading of the amount of the substance 30 using sensing and reporting device 20. A usage rate generally indicates an amount of substance 30 used over a period of time. The period of time may vary based on implementation. The period of time may be a standardized time, e.g., one day, one week, one month, etc., or a variable amount of time, such as the amount of time between access events. The usage rate could be adjusted by averaging it with previous rates or by summing the removed portions over a predetermined number of days, e.g., 30, and dividing the summed portions by the number of days.

Next, in step 510, an expected depletion date may be calculated based on the current amount of the substance and the usage rate of the substance. The expected depletion date would assume that the usage rate will be constant in the future and will calculate the number of remaining days worth of the substance 30. The depletion date could be based on time values other than days, such as weeks, hours, etc.

Next, in step 515, a replenishment date may be established based on the expected depletion date. The replenishment date does not necessarily need to be the expected depletion date. The replenishment date may be coordinated with the replenishment of multiple substances. For instance, there may be a standard or periodic time for reordering or shopping for a number of substances. Accordingly, it may be desirable to vary the replenishment date from the expected depletion date.

Next, in step 520, an expected unit cost may be associated with the substance. The expected unit cost generally represents a cost for a standardized unit quantity, e.g., oz., pound, gram, kilogram, liter, etc. Simple conversions may be used to normalize quantities having different units. The expected unit cost may be provided by a supplier of the substance. If more than one source of the substance is available, the expected unit cost may be an average of the unit costs from a set of the suppliers. In another exemplary approach, the expected unit cost may be an average unit cost of a set of previous replenishments of the substance. In still another exemplary approach, other inventory systems may provide the unit costs from previous replenishments. For instance, a centralized data store may contain the unit costs of previous replenishments from a plurality of inventories.

Next, in step 525, current price and quantity data of a provider of the substance may be received. For instance, the inventory system may be part of a networked communication system such that connections between the system and the provider of the substance may be established in order to receive current price and quantity data. The current price may be a promotional or sale price. The price may only be valid over a certain period of time. The end time for the promotion may be included with the price and quantity data. Including the end date for the promotional price may facilitate the adjustments to the replenishment date.

Next, in step 530, it may be determined whether the current unit price is less than the expected unit price. If necessary, the current unit price and the expected unit price may be converted to a normalized or common unit. Thereafter, the prices may be compared using a standard inequality statement that evaluates to a Boolean true or false value.

Next, in step 535, it may be determined whether the available capacity can accommodate the additional quantity that is currently available. The capacity may be based on the size of the container 16. However any additional storage capacity may also be considered. Even if the available capacity cannot immediately accommodate the additional quantity, the capacity may be increasing over time according to the usage rate. Accordingly, the end date of the promotional price may be considered to determine if there will be expected capacity in time to take advantage of the promotional price.

Next, in step 540, the replenishment date may be adjusted to take advantage of the current price. The current price may only be available for a certain number of days. The replenishment date could be moved forward to fall before the conclusion of the current price.

Following step 540, the process 500 may end. Accordingly, process 500 demonstrates exemplary steps to tracking usage rates and scheduling replenishments based on diminishing quantities and current prices. It is to be understood that the scheduling of replenishments may be severed from the above process such that process 500 could merely track usage rates. Similarly an aspect of tracking usage rates includes the tracking of current quantities of the substance 30 stored in container 16. Another exemplary inventory system may not be concerned with usage rates and may only be concerned with instantaneous or historical quantities. Accordingly, it is to be understood that the inventory system as disclosed could implement these and other inventory management functions.

Figure 11:
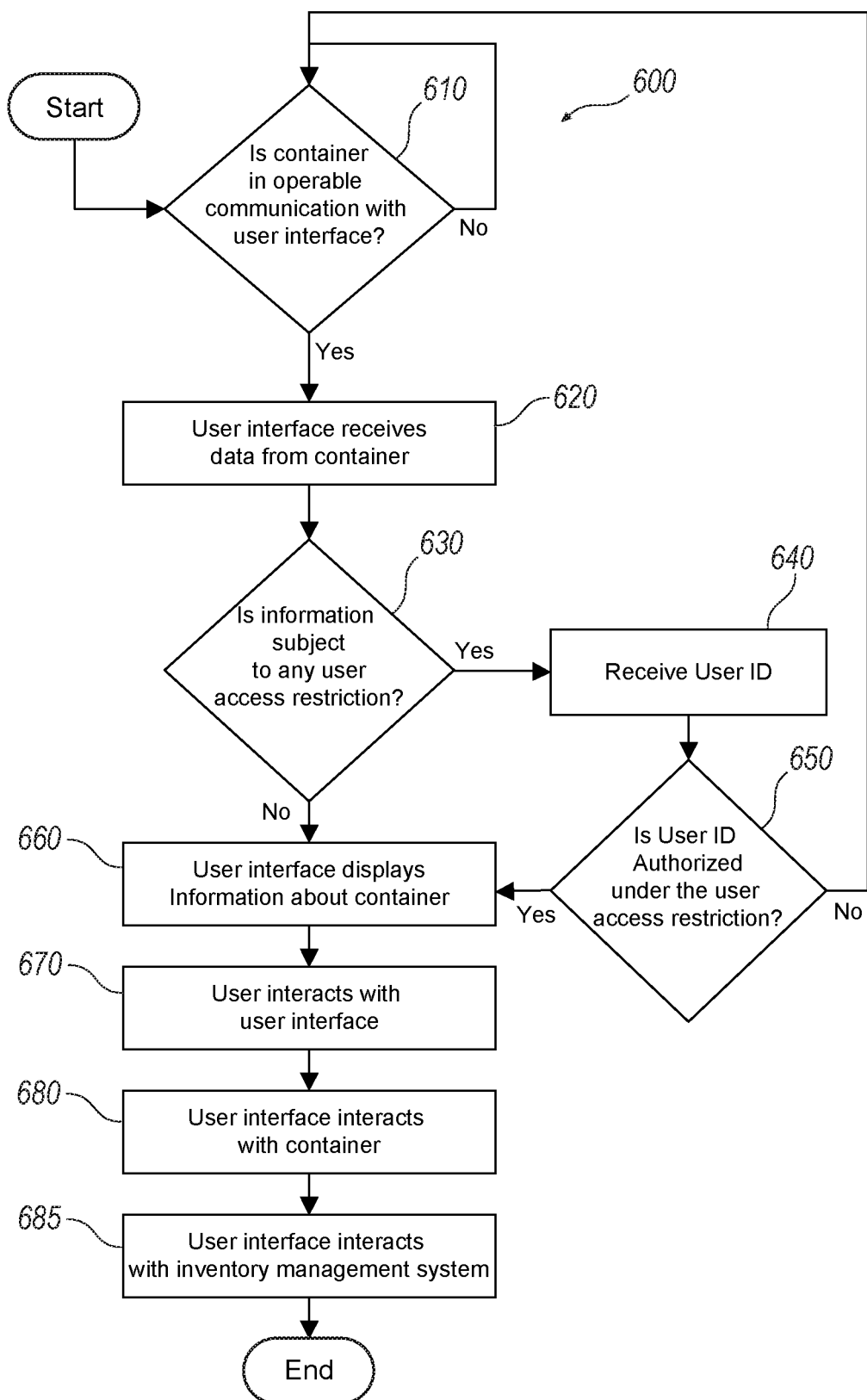
FIG. 11 is a flowchart depicting exemplary steps and procedures relating to an inventory management system interacting with a user interface.

FIG. 11 illustrates a flowchart with exemplary steps and decisions related to a process 600 for using a user interface in conjunction with a self reporting container 16.

Process 600 begins in step 610 where user interface waits for a container to initiate communication. It is to be understood that process 600 is a continuous process, so operable communication with a container may start at any time, including during the time that another communication is being processed. The user interface may ignore a second container that attempts to communicate with the user interface while the user interface is in operable communication with the first container or may be in operable communication with both containers.

Next, in step 620, the user interface may receive data from the container, such as an event notification. The event notification may be an access event. If the container is processing information locally, the data from the container could alternatively include any of the notifications described above in processes 200, 250, 300, 400 and 500. If the user interface is in operable communication with more than one container and receives a notification from a second container before it has completed processing a notification from a first container, the notifications may simultaneously processed or sequentially processed, or the user may be provided by the user interface with a notification of the two communications and an opportunity to select the manner of processing the two communications. Additionally, the data may include data generated as a result of a query sent to the container by the user interface.

Next, in step 630, it is determined if the event notification is subject to a user restriction or another form of authorization. For example, if the notification relates to access of a medicine, the privacy of the individual accessing the medicine may require authorization of the user of the user interface before the user may see the event notification.

If the information is subject to a user access restriction, the user interface may receive a user ID in step 640 and determine the authority of the user ID in step 650. If the user ID is not authorized, the data received by the user interface is not processed by the user interface. Alternatively, the data may be processed by the user interface in some manner or referred by the user interface to an inventory management system for some processing without providing the restricted information to the user.

If the information is not subject to a user restriction, or if the user ID is authorized to access the information, then the user interface displays information in step 660. The displayed information may be information about the event or the container derived from the event notification. The displayed information may be information derived by the user interface or a system in communication with the user interface from a calculation, look up table or other algorithm. The displayed information may be information derived by the user interface or a system in communication with the user interface by the application of rules, such as those described in the processes 200, 250, 300, 400 and 500.

Next, in step 670, the user may interact with the user interface, such as by making a query for information from the container, or providing an input of information for the container.

Next, in step 680, the user interface may interact with the container to make the query or provide the information to the container.

Next, in step 690, the user interface may further interact with the inventory management system to provide data to the inventory management system, such as to provide the inventory management system with event information used as input to any of the processes 200, 250, 300, 400 and 500 or to receive and communicate to the user any notification, such as any notification in any of these processes.

Following step 690, the process 600 may end. Accordingly, process 600 provides exemplary steps and decisions related to the use of a user interface in conjunction with self reporting containers of substance.

It should be noted that process 600 can be used for activation at the first introduction of a new container into an inventory management system or for the refilling of a container with a new substance. In this case, the container is first placed in operable communication with the user interface in step 610 by causing an event that brings the container to the attention of the user interface, such as an access event, by bringing the container into the range of a scanning device capable of reading data from the container, or by manually entering information into the user interface about the container.

In step 620, the user interface receives data from the container. The data received from the newly introduced container may be sufficient for the user interface to identify the container and its contents or more information may be required. The data may include as little as an identifier of the container or its contents or may include one or more of the type of substance in the container, the capacity of the container, the amount in the container, the date of filling the container, an expiration date, a time for disposal after first opening, a manufacturers name, a permitted user ID, usage restrictions, rules relevant to the contents, and other data about the contents and its use.

In step 660, the user interface displays data about the container or the event. The user interface may indicate that more information is needed or provide an opportunity to supplement, delete, or change any information.

Next, in step 670, the user interacts with the user interface by supplementing, editing or deleting the information provided by the user interface or by answering questions posed by the user interface. This supplemental information may include one or more of the type of substance in the container, the capacity of the container, the amount in the container, the date of filling the container, an expiration date, a time for disposal after first opening, a manufacturers name, a permitted user ID, usage restrictions, rules relevant to the contents, and other data about the contents and its use. The user may also pose one or more queries to the container or provide information for storage in a data system associated with the container.

Next, in step 680, the user interface may interact with the container to pose a query to the container, provide information for storage locally at the container, and receive answers to any query from the container.

Next, in step 690, the user interface may interact with the inventory management system to add the data about the newly added or newly filled container to the inventory management system. The inventory management system may supplement the information by using the information received from the user interface to access databases having more information about the container or the substance. For example, the inventory management system may use an identifier or other data to retrieve rules applicable to the contents or to retrieve expiration, pricing, dosage, warnings, recalls and other data applicable to the contents of the container.

FIG. 12 illustrates a flow chart with exemplary steps and decisions related to a process 700 for activating a container filled with the substance at the time of introduction a data management system.

Process 700 begins in step 710 where a user selects a container having a sensor and an identifier for introduction into the data management system. The container may be a new container that has not been used previously in the inventory system. Alternatively, the container may have been used previously and may now be reintroduced, for example, because a different substance is intended to be used or the old substance has been removed and fresher substance or substance with different attributes is intended to be used.

In step 715, the substance is added to the container.

In step 720, the identifier associated with the container, its sensor or transmitter, or the substance is communicated to the data processing system for the inventory management system.

In step 725, the identifier is associated in the inventory management system with the substance. This may occur automatically through a look up table or may be provided by the user through a user interface associated with the container or with the data processing system.

In step 730, the inventory management system retrieves additional data associated with the identifier or with the substance, for example from internet sources, from data read from the original packaging of the substance, or from data input by the user, either directly or by using an input device, such as a scanner, a camera or a microphone.

This additional data may include condition of the substance, initial conditions for the substance, data relating to the fill process, an attribute identifier of the substance, an attribute value of the substance, an attribute identifier of the sensor, an attribute value of the sensor, an attribute identifier of the container, an attribute value of the container, a notification trigger rule associated with the substance, historical information about the substance, usage instruction relating to the substance, dietary and allergenic information relating to the substance, purchasing information, advertising information, recipe information, supply chain information, ingredient information, usage information relating to the substance, or un-natural ingredient information such as information about pesticides, steroids, and fertilizers.

The additional information may include an image. The image may be a picture of the container, a picture of the user or owner of the container, a picture associated with the substance, its manufacture, use, features or advantages, or an icon associated in some manner with one of the container system members. The image may be associated in the data processing system with the container to facilitate future communication of information to the user by the data processing system.

Still other types of information that may be inputted include the name of a substance, its owner, its user or its manufacturer, a category of substance, and a calendar date and/or time associated with the substance or an event related to the substance.

FIG. 13 illustrates a flow chart with exemplary steps and decisions related to a process 750 for activating a container to which a transmitter is added at the use environment.

Process 750 starts with step 760 wherein a filled container that does not have a sensor or identifier is selected for introduction into an inventory management system.

In step 765, a sensor and transmitter, at least one of which has an identifier, is installed on or in the container. In step 770, the identifier is associated with the new contents. This can be accomplished locally at the container if the container has user input capability or can be accomplished by input into the data processing system for the inventory management system, for example, by direct user input or by permitting the data processing system to scan information printed on or otherwise associated with the container by its manufacturer. In step 775, the container is introduced into the use environment, permitting the data processing system to communicate with the transmitter. It will be appreciated that in some cases, steps 765 and 770 can occur in reverse order. It will also be appreciated that additional user input and retrieval may be used, as described for process 700, as shown in step 780.

Figure 14:
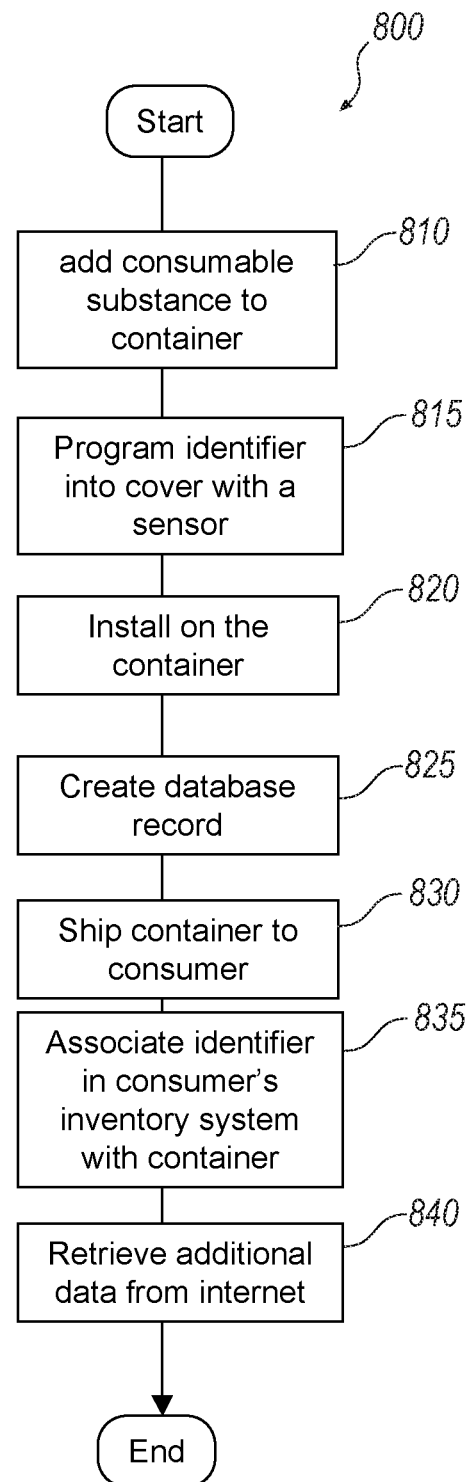
FIG. 14 is a flow chart depicting exemplary steps in activating a container to which a transmitter is added at the time of adding substance, which is not necessarily introduced immediately into the use environment.

FIG. 14 illustrates a flow chart with exemplary steps and decisions related to a process 800 for activating a container to which a transmitter is added at the time of adding substance, which is not necessarily introduced immediately into the use environment. For example, process 800 may be used to activate a container of substance that is filled by a manufacturer into a container with a sensor and transmitter in the cover prior to shipping the container to the customer.

In step 810, a container is filled with a consumable substance by a manufacturer. Next, in step 815 an identifier is programmed into the sensor or transmitter in the cover that will be used with the container. Next, in step 820 the cover is installed on the container. In step 825, a database record is created by the manufacturer that associates the identifier with the substance, the container and other information that may be useful for the manufacturer and a consumer. In step 830, the container is acquired by a consumer. In step 835, the consumer introduces the container into a use environment with an inventory management system and the identifier is associated with the container and the substance, such as by one of the methods previously described. In step 840, the inventory management system retrieves information about the container or the substance from the manufacturer's database by using the identifier provided by the manufacturer.

It is anticipated that the steps of process 800 may be varied from that described above. For example, step 815 can occur before or after step 810. Step 820 may occur before or after step 815 but must occur after step 810. Step 825 can occur at any time prior to step 840.

The present invention has been particularly shown and described with reference to the foregoing embodiments, which are merely illustrative of the best modes for carrying out the invention. It should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

What is claimed is:

1. A system comprising:
   a refrigerator;
   a container within the refrigerator for storing a substance and comprising a sensing and reporting system configured to determine an amount of substance within the container, wherein the sensing and reporting system comprises:
      a sensor configured to sense the amount of substance in the container;
      a transmitter in communication with a remote device; and
      a processor in communication with the sensor and the transmitter;
   wherein, upon moving the container, the processor is configured to:
      activate the sensor to sense the amount of substance in the container and provide an indication of the sensed amount of substance in the container to the processor; and
      activate the transmitter to transmit the indication of the amount of substance to the remote device, and
      wherein the sensing and reporting system is further configured to sense a squeezing of the container.

2. The system of claim 1, wherein the sensing and reporting system further comprises a memory storage device which holds at least one element of data, wherein, upon an access event at the container, the processor is configured to activate the transmitter to further transmit the at least one element of data to the remote device.

3. The system of claim 2, wherein the at least one element of data includes at least one of:
   an indication of a prior amount of the substance within the container;
   an indication of a chemical component of the substance within the container;
   a time that the container was first opened by a user;
   a time that the container was last opened;
   a time that the container was first filled with substance;
   a name of a producer of the substance within the container;
   a trade name of the substance within the container;
   a generic name of the substance within the container;
   an identifier of a processing facility that processed the substance within the container;
   a batch number of the substance within the container;

a processing date of the substance within the container;

an indication of a nutritional attribute of the substance within the container;

an indication of a presence of allergens associated with the substance within the container;

a lookup table mapping the indication of the sensed attribute to the amount of the substance within the container;

an indication of a physical dimension of the container;

a history of the amounts of the substance within the container;

a control parameter for an accessory module;

an indication of a dosage of the substance within the container;

an indication of an ideal environmental condition of the substance within the container;

information about a physical characteristic of the substance within the container;

an indication of a permitted user of the substance within the container; and an output from an additional sensor.

4. The system of claim 1, wherein the sensing and reporting system further includes a memory storage device which stores an identifier uniquely identifying the container, wherein, upon an access event at the container, the processor is configured to activate the transmitter to further transmit the identifier to the remote device.

5. The system of claim 1, wherein the sensing and reporting system further includes a power source providing electrical power to the sensor, the transmitter, and the processor.

6. The system of claim 1, wherein the sensing and reporting system further includes a receiver for bi-directional communication with the remote device.

7. The system of claim 1, wherein the transmitter comprises a transceiver and includes a receiver for bi-directional communication with the remote device.

8. The system of claim 1, wherein the sensing and reporting system includes multiple sensors.

9. The system of claim 1, wherein the sensor is configured to sense a distance between the sensor and a level of the substance within the container.

10. The system of claim 1, wherein the sensor comprises one of an acoustic sensor, a capacitance sensor, an infrared sensor, an inductive sensor, a resistive sensor, an evaporative gas sensor, an image sensor, a pressure sensor, a float sensor, a strain gauge sensor, or a force sensor.

11. The system of claim 1, wherein the transmitter comprises a wireless transmitter in wireless communication with the remote device.

12. The system according to claim 11, wherein the transmitter uses a standard comprising at least one of Bluetooth®, Zigbee® Wibree™, enOcean®, Z-wave®, wi-fi, and wi-max.

13. The system of claim 1, wherein the container further includes at least one of a motor, an agitator, a fan, a dispenser, a dryer, a pump, a cooler, a heater, or an ozone generator.

14. The system of claim 1, wherein the container further includes an active device configured to affect an environment inside the container.

15. The system of claim 1, wherein the container further includes a user authorization module.

16. The system of claim 1, wherein the container further includes a common enclosure housing the sensing and reporting system.

17. A system comprising:

a refrigerator;

a container within the refrigerator for storing a substance and comprising a sensing and reporting system configured to determine an amount of the substance within the container, wherein the sensing and reporting system comprises:

a sensor configured to sense the amount of the substance;

a transmitter;

a processor in communication with the sensor and the transmitter; and a control unit in communication with the transmitter of the sensing and reporting system, and comprising a visual display and a control interface, and wherein the sensing and reporting system is further configured to sense a squeezing of the container.

18. The system of claim 17, wherein the control unit comprises a receiver and a transmitter for receiving communications from transmitter of sensing and reporting device.

19. The system of claim 17, wherein, upon an access event at the container, the processor is configured to:

activate the sensor to sense the amount of the substance and provide an indication of the amount of the substance to the processor; and activate the transmitter to transmit the indication of the sensed attribute to the control unit.

* * * * *